(12) United States Patent
Kato et al.

(10) Patent No.: US 11,687,196 B2
(45) Date of Patent: Jun. 27, 2023

(54) DETECTION DEVICE, FINGERPRINT DETECTION DEVICE, AND VEIN DETECTION DEVICE

(71) Applicant: Japan Display Inc., Tokyo (JP)

(72) Inventors: Hirofumi Kato, Tokyo (JP); Ayato Kitamura, Tokyo (JP)

(73) Assignee: Japan Display Inc., Tokyo (JP)

(*) Notice: Subject to any disclaimer, the term of this patent is extended or adjusted under 35 U.S.C. 154(b) by 0 days.

(21) Appl. No.: 17/951,296

(22) Filed: Sep. 23, 2022

(65) Prior Publication Data

US 2023/0015361 A1  Jan. 19, 2023

Related U.S. Application Data

(63) Continuation of application No. PCT/JP2021/010814, filed on Mar. 17, 2021.

(30) Foreign Application Priority Data

Mar. 27, 2020  (JP) ................................ 2020-059056

(51) Int. Cl.
*G06V 40/13* (2022.01)
*G06F 3/042* (2006.01)
*G09G 3/36* (2006.01)

(52) U.S. Cl.
CPC ............ *G06F 3/0421* (2013.01); *G06V 40/13* (2022.01); *G09G 3/3611* (2013.01)

(58) Field of Classification Search
CPC .... G06F 3/0421; G06V 40/13; G09G 3/3611; A61B 5/1172; G06T 1/00
See application file for complete search history.

(56) References Cited

U.S. PATENT DOCUMENTS 9,064,460 B2 * 6/2015 Sugita .................. G09G 3/3406
2009/0027358 A1  1/2009 Hosono
(Continued)

FOREIGN PATENT DOCUMENTS

JP  2009-032005 A   2/2009
JP  2019-174963 A  10/2019
WO  WO2011/065555 A1  6/2011

OTHER PUBLICATIONS

International Search Report issued in International Patent Application No. PCT/JP2021/010814 dated Jun. 1, 2021 and English translation of same. 5 pages.
(Continued)

*Primary Examiner* — Jonathan A Boyd
(74) *Attorney, Agent, or Firm* — K&L Gates LLP

(57) ABSTRACT

A detection device includes: optical sensors; switching elements, gate lines, and signal lines corresponding to the optical sensors; a detection circuit that is supplied with signals from the optical sensors through the signal lines; and a signal line selection circuit for switching a coupling state between the signal lines and the detection circuit. A drive signal is supplied to the gate lines row by row to bring the switching elements belonging to a predetermined row into a coupled state. The signal line selection circuit couples the signal lines to the detection circuit column by column in a predetermined order in a reading period of the predetermined row. A reset potential is supplied to the optical sensors and the signal lines belonging to the predetermined row after completion of the reading period of the predetermined row and before start of the reading period of a row next to the predetermined row.

7 Claims, 18 Drawing Sheets

(56) References Cited

U.S. PATENT DOCUMENTS

| | | | |
|---|---|---|---|
| 2012/0188207 A1* | 7/2012 | Usukura | G09G 3/3648 |
| | | | 345/175 |
| 2012/0280939 A1* | 11/2012 | Ahn | G06F 3/042 |
| | | | 345/175 |
| 2019/0088184 A1* | 3/2019 | Morein | G06F 3/04166 |
| 2021/0012082 A1 | 1/2021 | Uchida et al. | |

OTHER PUBLICATIONS

Written Opinion issued in International Patent Application No. PCT/JP2021/010814 dated Jun. 1, 2021. 3 pages.

* cited by examiner

FIG.18

(TABLE 1)

|  | T11 T12 T13 T14 T15 T16 |
|---|---|
| FRAME 1 | ASW1 → ASW2 → ASW3 → ASW4 → ASW5 → ASW6 |
| FRAME 2 | ASW2 → ASW3 → ASW4 → ASW5 → ASW6 → ASW1 |
| FRAME 3 | ASW3 → ASW4 → ASW5 → ASW6 → ASW1 → ASW2 |
| FRAME 4 | ASW4 → ASW5 → ASW6 → ASW1 → ASW2 → ASW3 |
| FRAME 5 | ASW5 → ASW6 → ASW1 → ASW2 → ASW3 → ASW4 |
| FRAME 6 | ASW6 → ASW1 → ASW2 → ASW3 → ASW4 → ASW5 |

DETECTION DEVICE, FINGERPRINT DETECTION DEVICE, AND VEIN DETECTION DEVICE

CROSS-REFERENCE TO RELATED APPLICATION

This application claims the benefit of priority from Japanese Patent Application No. 2020-059056 filed on Mar. 27, 2020 and International Patent Application No. PCT/JP2021/010814 filed on Mar. 17, 2021, the entire contents of which are incorporated herein by reference.

BACKGROUND

1. Technical Field

What is disclosed herein relates to a detection device, a fingerprint detection device, and a vein detection device.

2. Description of the Related Art

Optical sensors capable of detecting fingerprint patterns and vascular patterns are known (for example, Japanese Patent Application Laid-open Publication No. 2009-032005).

In a detection method of scanning a plurality of optical sensors to sequentially read output signals from the sensors, the order of the scanning and variations in the timing of resetting the optical sensors may cause variations in the detected output signals.

For the foregoing reasons, there is a need for a detection device, a fingerprint detection device, and a vein detection device capable of improving the detection accuracy.

SUMMARY

According to an aspect, a detection device includes: a plurality of optical sensors arranged in a matrix having a row-column configuration; a plurality of switching elements, a plurality of gate lines, and a plurality of signal lines provided corresponding to the optical sensors; a detection circuit configured to be supplied with signals from the optical sensors through the signal lines; and a signal line selection circuit configured to switch a coupling state between the signal lines and the detection circuit. A drive signal is supplied to the gate lines row by row to bring the switching elements belonging to a predetermined row into a coupled state. The signal line selection circuit is configured to couple the signal lines to the detection circuit column by column in a predetermined order in a reading period of the predetermined row. A reset potential is supplied to the optical sensors and the signal lines belonging to the predetermined row after completion of the reading period of the predetermined row and before start of the reading period of a row next to the predetermined row.

According to an aspect, a fingerprint detection device includes the detection device and at least one or more light sources.

According to an aspect, a vein detection device includes the detection device and at least one or more light sources.

BRIEF DESCRIPTION OF THE DRAWINGS

FIG. 18 is a table illustrating orders of coupling of signal lines for each of one frame detections.

DETAILED DESCRIPTION

Figure 1:
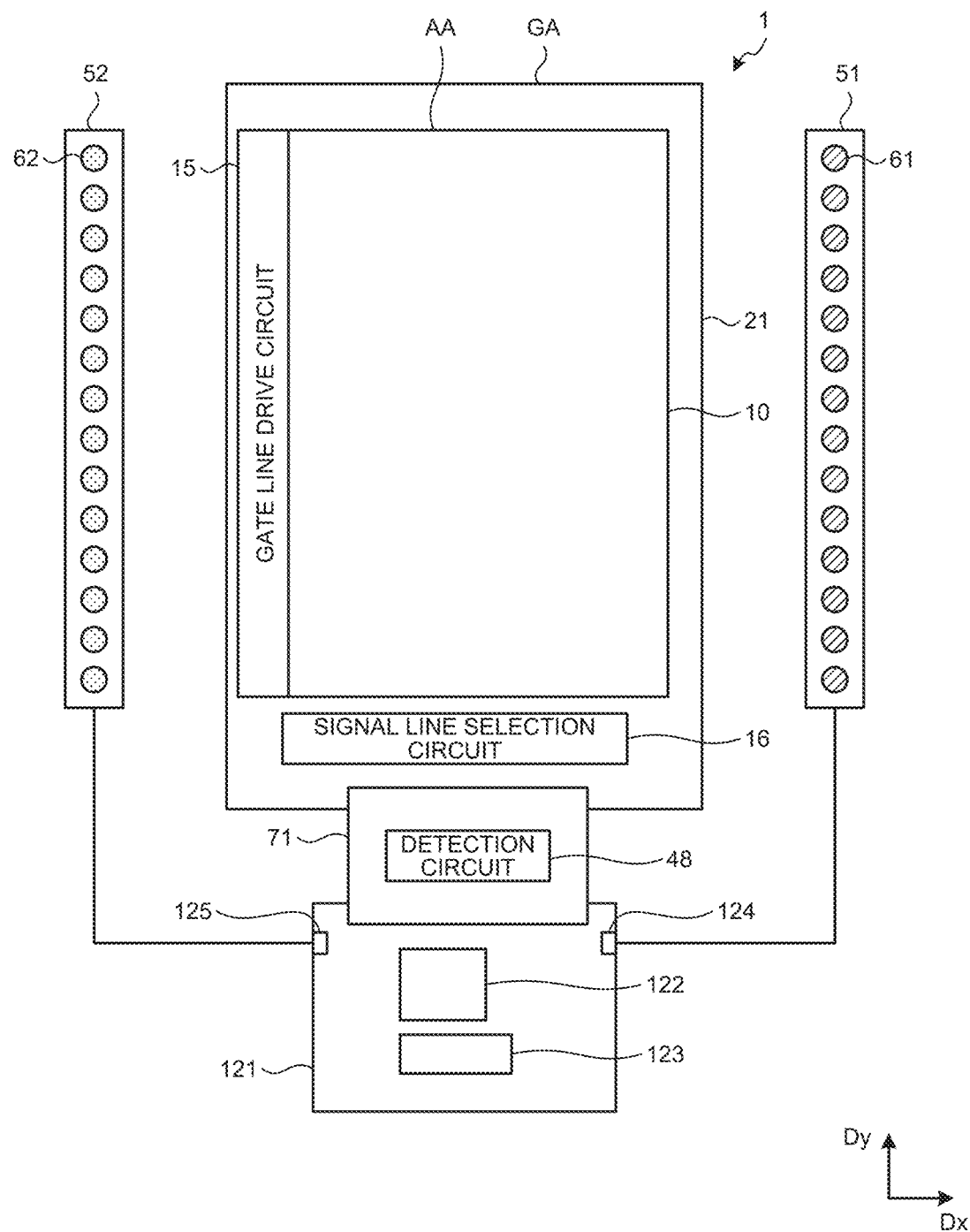
FIG. 1 is a plan view illustrating a detection device according to a first embodiment.

The following describes modes (embodiments) for carrying out the present disclosure in detail with reference to the drawings. The present disclosure is not limited to the description of the embodiments given below. Components described below include those easily conceivable by those skilled in the art or those substantially identical thereto. In addition, the components described below can be combined as appropriate. What is disclosed herein is merely an example, and the present disclosure naturally encompasses appropriate modifications easily conceivable by those skilled in the art while maintaining the gist of the disclosure. To further clarify the description, the drawings may schematically illustrate, for example, widths, thicknesses, and shapes of various parts as compared with actual aspects thereof. However, they are merely examples, and interpretation of the present disclosure is not limited thereto. The same component as that described with reference to an already mentioned drawing is denoted by the same reference numeral through the description and the drawings, and detailed description thereof may not be repeated where appropriate.

In this disclosure, when an element is described as being "on" another element, the element can be directly on the other element, or there can be one or more elements between the element and the other element.

First Embodiment

FIG. 1 is a plan view illustrating a detection device according to a first embodiment. As illustrated in FIG. 1, a detection device 1 includes a sensor base member 21, a sensor 10, a gate line drive circuit 15, a signal line selection circuit 16, a detection circuit 48, a control circuit 122, a power supply circuit 123, a first light source base member 51, a second light source base member 52, first light sources 61, and second light sources 62. The first light source base member 51 is provided with the first light sources 61. The second light source base member 52 is provided with the second light sources 62.

The sensor base member 21 is electrically coupled to a control substrate 121 through a flexible printed circuit board 71. The flexible printed circuit board 71 is provided with the detection circuit 48. The control substrate 121 is provided with the control circuit 122 and the power supply circuit 123. The control circuit 122 is, for example, a field-programmable gate array (FPGA). The control circuit 122 supplies control signals to the sensor 10, the gate line drive circuit 15, and the signal line selection circuit 16 to control a detection operation of the sensor 10. The control circuit 122 supplies control signals to the first and the second light sources 61 and 62 to control lighting and non-lighting of the first and the second light sources 61 and 62. The power supply circuit 123 supplies voltage signals including, for example, a sensor power supply signal (sensor power supply voltage) VDDSNS (refer to FIG. 4) to the sensor 10, the gate line drive circuit 15, and the signal line selection circuit 16. The power supply circuit 123 supplies a power supply voltage to the first and the second light sources 61 and 62.

The sensor base member 21 has a detection area AA and a peripheral area GA. The detection area AA is an area provided with a plurality of optical sensors PD (refer to FIG. 4) included in the sensor 10. The peripheral area GA is an area between the outer perimeter of the detection area AA and ends of the sensor base member 21 and is an area not provided with the optical sensors PD.

The gate line drive circuit 15 and the signal line selection circuit 16 are provided in the peripheral area GA. Specifically, the gate line drive circuit 15 is provided in an area extending along a second direction Dy in the peripheral area GA. The signal line selection circuit 16 is provided in an area extending along a first direction Dx in the peripheral area GA, and is provided between the sensor 10 and the detection circuit 48.

The first direction Dx is one direction in a plane parallel to the sensor base member 21. The second direction Dy is one direction in the plane parallel to the sensor base member 21 and is a direction orthogonal to the first direction Dx. The second direction Dy may non-orthogonally intersect the first direction Dx. A third direction Dz is a direction orthogonal to the first direction Dx and the second direction Dy and is a direction normal to the sensor base member 21.

The first light sources 61 are provided on the first light source base member 51 and are arranged along the second direction Dy. The second light sources 62 are provided on the second light source base member 52 and are arranged along the second direction Dy. The first light source base member 51 and the second light source base member 52 are electrically coupled, through respective terminals 124 and 125 provided on the control substrate 121, to the control circuit 122 and the power supply circuit 123.

For example, inorganic light-emitting diodes (LEDs) or organic electroluminescent (EL) diodes (organic light-emitting diodes: OLEDs) are used as the first and the second light sources 61 and 62. The first and the second light sources 61 and 62 emit first and second light, respectively, having different wavelengths.

The first light emitted from the first light sources 61 is mainly reflected on a surface of an object to be detected, such as a finger Fg, and is incident on the sensor 10. As a result, the sensor 10 can detect a fingerprint by detecting a shape of asperities on the surface of the finger Fg or the like. The second light emitted from the second light sources 62 is mainly reflected in the finger Fg or the like, or transmitted through the finger Fg or the like, and is incident on the sensor 10. As a result, the sensor 10 can detect information on a living body in the finger Fg or the like. Examples of the information on the living body include a pulse wave, pulsation, and a vascular image of the finger Fg or a palm. That is, the detection device 1 may be configured as a fingerprint detection device to detect a fingerprint or a vein detection device to detect a vascular pattern of, for example, veins.

The first light may have a wavelength of from 500 nm to 600 nm, for example, a wavelength of approximately 550 nm, and the second light may have a wavelength of from 780 nm to 950 nm, for example, a wavelength of approximately 850 nm. In this case, the first light is blue or green visible light, and the second light is infrared light. The sensor 10 can detect a fingerprint based on the first light emitted from the first light sources 61. The second light emitted from the second light sources 62 is reflected in the object to be detected such as the finger Fg, or transmitted through or absorbed by the finger Fg or the like, and is incident on the sensor 10. As a result, the sensor 10 can detect the pulse wave or the vascular image (vascular pattern) as the information on the living body in the finger Fg or the like.

Alternatively, the first light may have a wavelength of from 600 nm to 700 nm, for example, approximately 660 nm, and the second light may have a wavelength of from 780 nm to 900 nm, for example, approximately 850 nm. In this case, the sensor 10 can detect a blood oxygen saturation level in addition to the pulse wave, the pulsation, and the vascular image as the information on the living body based on the first light emitted from the first light sources 61 and the second light emitted from the second light sources 62. Thus, the detection device 1 includes the first and the second light sources 61 and 62, and therefore, can detect the various information on the living body by performing the detection based on the first light and the detection based on the second light.

The arrangement of the first and the second light sources 61 and 62 illustrated in FIG. 1 is merely an example, and may be changed as appropriate. The detection device 1 is provided with a plurality of types of light sources (first and second light sources 61 and 62) as the light sources. However, the light sources are not limited thereto and may be of one type. For example, the first and the second light sources 61 and 62 may be arranged on each of the first light source base member 51 and the second light source base member 52. The first and the second light sources 61 and 62 may be provided on one or three or more light source base members. Alternatively, only at least one light source needs to be disposed.

Figure 2:
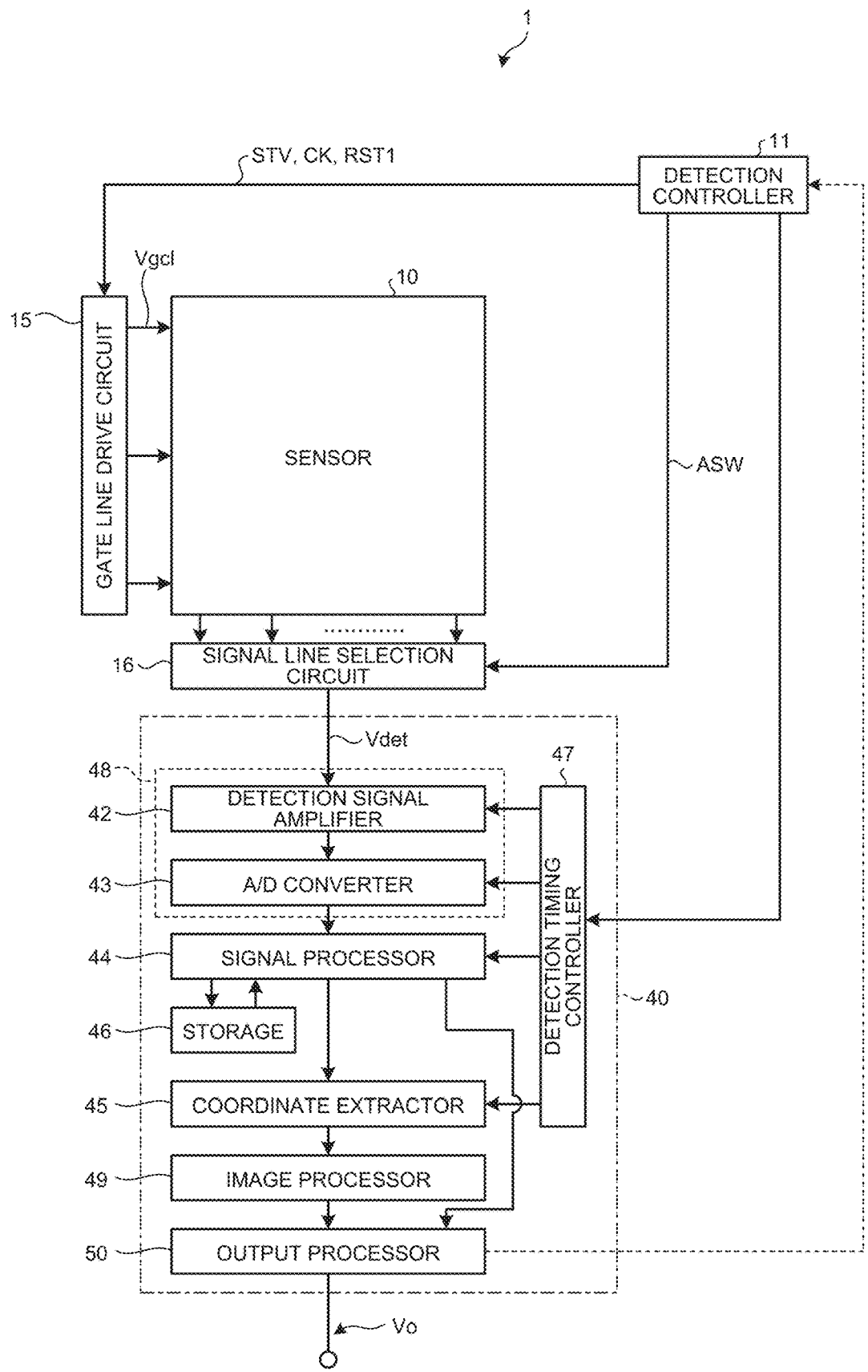
FIG. 2 is a block diagram illustrating a configuration example of the detection device according to the first embodiment.

FIG. 2 is a block diagram illustrating a configuration example of the detection device according to the first embodiment. As illustrated in FIG. 2, the detection device 1 further includes a detection controller (detection control circuit) 11 and a detector (detection signal processing circuit) 40. The control circuit 122 includes one, some, or all functions of the detection controller 11. The control circuit 122 also includes one, some, or all functions of the detector 40 except those of the detection circuit 48.

The sensor 10 includes the optical sensors PD. Each of the optical sensors PD included in the sensor 10 is a photodiode, and outputs an electrical signal corresponding to light emitted thereto as a detection signal Vdet to the signal line selection circuit 16. The sensor 10 performs the detection in response to a gate drive signal Vgcl supplied from the gate line drive circuit 15.

The detection controller 11 is a circuit that supplies respective control signals to the gate line drive circuit 15, the signal line selection circuit 16, and the detector 40 to control operations thereof. The detection controller 11 supplies various control signals such as a start signal STV, a clock signal CK, and a reset signal RST1 to the gate line drive circuit 15. The detection controller 11 also supplies various control signals such as a selection signal ASW to the signal line selection circuit 16. The detection controller 11 supplies various control signals to the first and the second light sources 61 and 62 to control the lighting and non-lighting of the respective first and second light sources 61 and 62.

The gate line drive circuit 15 is a circuit that drives a plurality of gate lines GCL (refer to FIG. 3) based on the various control signals. The gate line drive circuit 15 sequentially or simultaneously selects the gate lines GCL, and supplies the gate drive signals Vgcl to the selected gate lines GCL. By this operation, the gate line drive circuit 15 selects the optical sensors PD coupled to the gate lines GCL.

Figure 3:
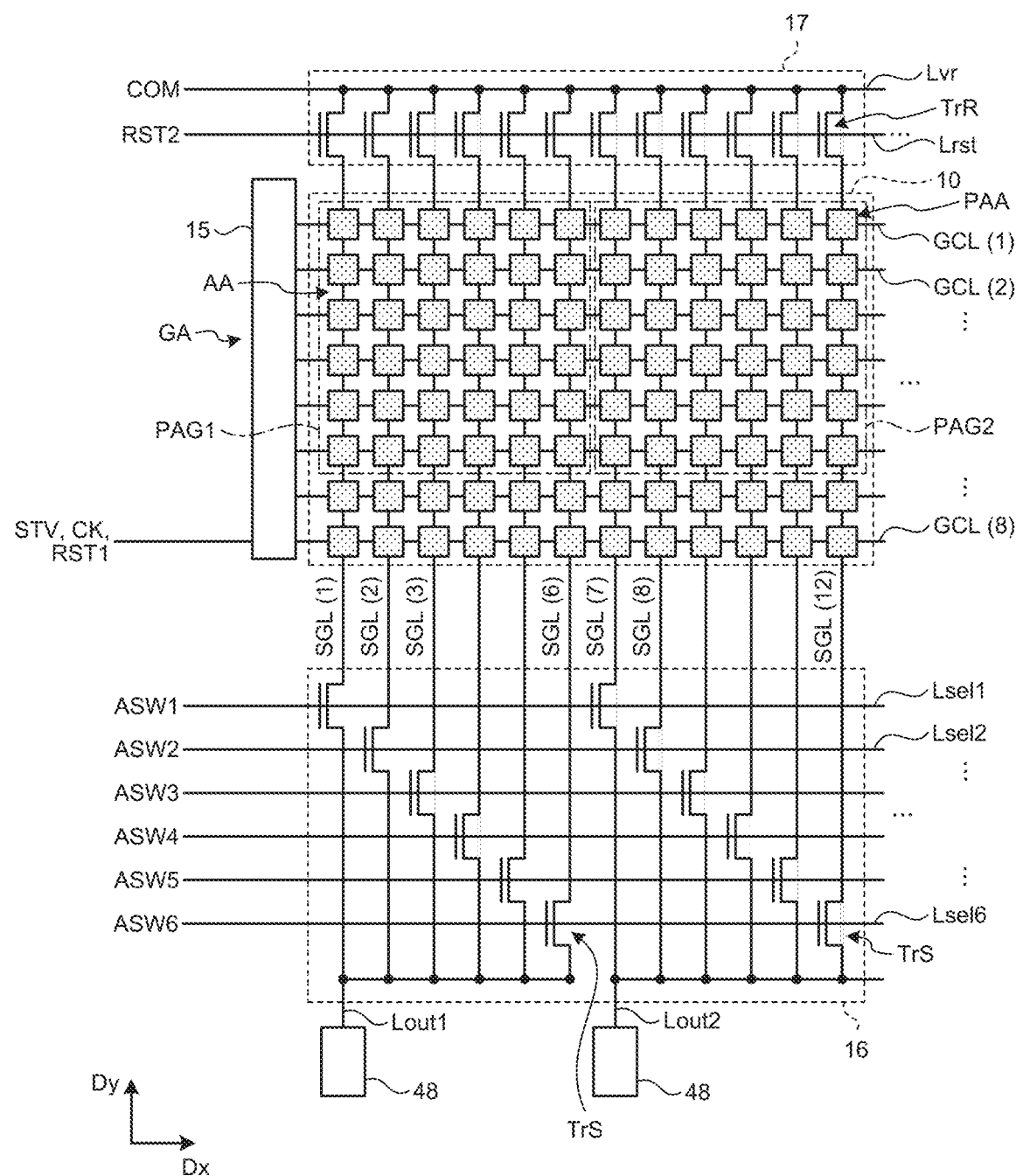
FIG. 3 is a circuit diagram illustrating the detection device.

The signal line selection circuit 16 is a switch circuit that sequentially or simultaneously selects a plurality of signal lines SGL (refer to FIG. 3). The signal line selection circuit 16 is, for example, a multiplexer. The signal line selection circuit 16 couples the selected signal lines SGL to the detection circuit 48 based on the selection signal ASW supplied from the detection controller 11. By this operation, the signal line selection circuit 16 outputs the detection signals Vdet of the optical sensors PD to the detector 40.

The detector 40 includes the detection circuit 48, a signal processor (signal processing circuit) 44, a coordinate extractor (coordinate extraction circuit) 45, a storage (storage circuit) 46, a detection timing controller (detection timing control circuit) 47, an image processor (image processing circuit) 49, and an output processor (output processing circuit) 50. Based on a control signal supplied from the detection controller 11, the detection timing controller 47 controls the detection circuit 48, the signal processor 44, the coordinate extractor 45, and the image processor 49 so as to operate in synchronization with one another.

The detection circuit 48 is, for example, an analog front-end (AFE) circuit. The detection circuit 48 is a signal processing circuit having functions of at least a detection signal amplifier 42 and an analog-to-digital (A/D) converter 43. The detection signal amplifier 42 amplifies the detection signals Vdet. The A/D converter 43 converts analog signals output from the detection signal amplifier 42 into digital signals.

The signal processor 44 is a logic circuit that detects a predetermined physical quantity received by the sensor 10 based on an output signal of the detection circuit 48. The signal processor 44 can detect the asperities on the surface of the finger Fg or the palm based on the signals from the detection circuit 48 when the finger Fg is in contact with or in proximity to a detection surface. The signal processor 44 can also detect the information on the living body based on the signal from the detection circuit 48. Examples of the information on the living body include the vascular image, the pulse wave, the pulsation, and the blood oxygen level of the finger Fg or the palm.

The signal processor 44 may also perform processing of acquiring the detection signals Vdet (information on the living body) simultaneously detected by the optical sensors PD, and averaging the detection signals Vdet. In this case, the detector 40 can perform stable detection by reducing measurement errors caused by noise or relative positional misalignment between the object to be detected, such as the Fg finger, and the sensor 10.

The storage 46 temporarily stores therein signals calculated by the signal processor 44. The storage 46 may be, for example, a random-access memory (RAM) or a register circuit.

The coordinate extractor 45 is a logic circuit that obtains detected coordinates of the asperities on the surface of the finger or the like when the contact or the proximity of the finger is detected by the signal processor 44. The coordinate extractor 45 is also a logic circuit that obtains detected coordinates of blood vessels of the finger Fg or the palm. The image processor 49 combines the detection signals Vdet output from the respective optical sensors PD of the sensor 10 to generate two-dimensional information indicating the shape of the asperities on the surface of the finger Fg or the like and two-dimensional information indicating the shape of the blood vessels of the finger Fg or the palm. The coordinate extractor 45 may output the detection signals Vdet as sensor outputs Vo instead of calculating the detected coordinates. A case can be considered where the detector 40 does not include the coordinate extractor 45 and the image processor 49.

The output processor 50 serves as a processor that performs processing based on the outputs from the optical sensors PD. Specifically, the output processor 50 of the embodiment outputs the sensor outputs Vo including at least pulse wave data based on at least the detection signals Vdet acquired through the signal processor 44. In the embodiment, the signal processor 44 outputs data indicating a variation (amplitude) in output of the detection signal Vdet of each of the optical sensors PD (to be described later), and the output processor 50 determines which outputs are to be employed as the sensor outputs Vo. However, the signal processor 44 or the output processor 50 may perform both these operations. The output processor 50 may include, for example, the detected coordinates obtained by the coordinate extractor 45 and the two-dimensional information generated by the image processor 49 in the sensor outputs Vo. The function of the output processor 50 may be integrated into another component (such as the image processor 49).

The following describes a circuit configuration example of the detection device 1. FIG. 3 is a circuit diagram illustrating the detection device. As illustrated in FIG. 3, the sensor 10 has a plurality of partial detection areas PAA arranged in a matrix having a row-column configuration. Each of the partial detection areas PAA is provided with the optical sensor PD.

The gate lines GCL extend in the first direction Dx, and are coupled to the partial detection areas PAA arranged in the first direction Dx. A plurality of gate lines GCL(1), GCL(2), ..., GCL(8) are arranged in the second direction Dy, and are each coupled to the gate line drive circuit 15. In the following description, the gate lines GCL(1), GCL(2), ..., GCL(8) will each be simply referred to as the gate line GCL when they need not be distinguished from one another. For ease of understanding of the description, FIG. 3 illustrates eight gate lines GCL. However, this is merely an example, and M gate lines GCL (where M is eight or larger, and is, for example, 256) may be arranged.

The signal lines SGL extend in the second direction Dy, and are coupled to the optical sensors PD of the partial detection areas PAA arranged in the second direction Dy. A plurality of signal lines SGL(1), SGL(2), ..., SGL(12) are arranged in the first direction Dx, and are each coupled to the signal line selection circuit 16 and a reset circuit 17. In the following description, the signal lines SGL(1), SGL(2), ..., SGL(12) will each be simply referred to as the signal line SGL when they need not be distinguished from one another.

For ease of understanding of the description, 12 signal lines SGL are illustrated. However, this is merely an example, and N signal lines SGL (where N is 12 or larger and is, for example, 252) may be arranged. In FIG. 3, the sensor 10 is provided between the signal line selection circuit 16 and the reset circuit 17. The present disclosure is not limited thereto. The signal line selection circuit 16 and the reset circuit 17 may be coupled to ends of the signal lines SGL in the same direction. The substantial area of one sensing region is, for example, substantially 50×50 µm². The resolution of the detection area AA is, for example, substantially 508 pixels per inch (ppi). The number of the sensing regions arranged in the detection area AA is, for example, 252 cells×256 cells. The area of the detection area AA is, for example, 12.6×12.8 mm².

The gate line drive circuit 15 receives the various control signals such as the start signal STV, the clock signal CK, and the reset signal RST1 from the control circuit 122 (refer to FIG. 1). The gate line drive circuit 15 sequentially selects the gate lines GCL(1), GCL(2), ..., GCL(8) in a time-division manner based on the various control signals. The gate line drive circuit 15 supplies the gate drive signal Vgcl to the selected one of the gate lines GCL. This operation supplies the gate drive signal Vgcl to a plurality of first switching elements Tr coupled to the gate line GCL, and corresponding ones of the partial detection areas PAA arranged in the first direction Dx are selected as detection targets.

The gate line drive circuit 15 may perform different driving for each of detection modes including the detection of a fingerprint and the detection of different items of the information on the living body (such as the pulse wave, the pulsation, the blood vessel image, and the blood oxygen level). For example, the gate line drive circuit 15 may drive more than one of the gate lines GCL collectively.

The signal line selection circuit 16 includes a plurality of selection signal lines Lsel, a plurality of output signal lines Lout, and third switching elements TrS. The third switching elements TrS are provided corresponding to the signal lines SGL. Six signal lines SGL(1), SGL(2), ..., SGL(6) are coupled to a common output signal line Lout1. Six signal lines SGL(7), SGL(8), ..., SGL(12) are coupled to a common output signal line Lout2. The output signal lines Lout1 and Lout2 are each coupled to the detection circuit 48.

The signal lines SGL(1), SGL(2), ..., SGL(6) are grouped into a first signal line block, and the signal lines SGL(7), SGL(8), ..., SGL(12) are grouped into a second signal line block. The selection signal lines Lsel are coupled to the gates of the respective third switching elements TrS included in one of the signal line blocks. One of the selection signal lines Lsel is coupled to the gates of the third switching elements TrS in the signal line blocks.

The control circuit 122 (refer to FIG. 1) sequentially supplies the selection signal ASW to the selection signal lines Lsel. This operation causes the signal line selection circuit 16 to operate the third switching elements TrS to sequentially select the signal lines SGL in one of the signal line blocks in a time-division manner.

The signal line selection circuit 16 selects one of the signal lines SGL in each of the signal line blocks. With the above-described configuration, the detection device 1 can reduce the number of integrated circuits (ICs) including the detection circuit 48 or the number of terminals of the ICs. The signal line selection circuit 16 may couple more than one of the signal lines SGL collectively to the detection circuit 48.

As illustrated in FIG. 3, the reset circuit 17 includes a reference signal line Lvr, a reset signal line Lrst, and fourth switching elements TrR. The fourth switching elements TrR are provided correspondingly to the signal lines SGL. The reference signal line Lvr is coupled to either the sources or the drains of the fourth switching elements TrR. The reset signal line Lrst is coupled to the gates of the fourth switching elements TrR.

The control circuit 122 supplies a reset signal RST2 to the reset signal line Lrst. This operation turns on the fourth switching elements TrR to electrically couple the signal lines SGL to the reference signal line Lvr. The power supply circuit 123 supplies a reference signal COM to the reference signal line Lvr. This operation supplies the reference signal COM to a capacitive element Ca (refer to FIG. 4) included in each of the partial detection areas PAA.

Figure 4:
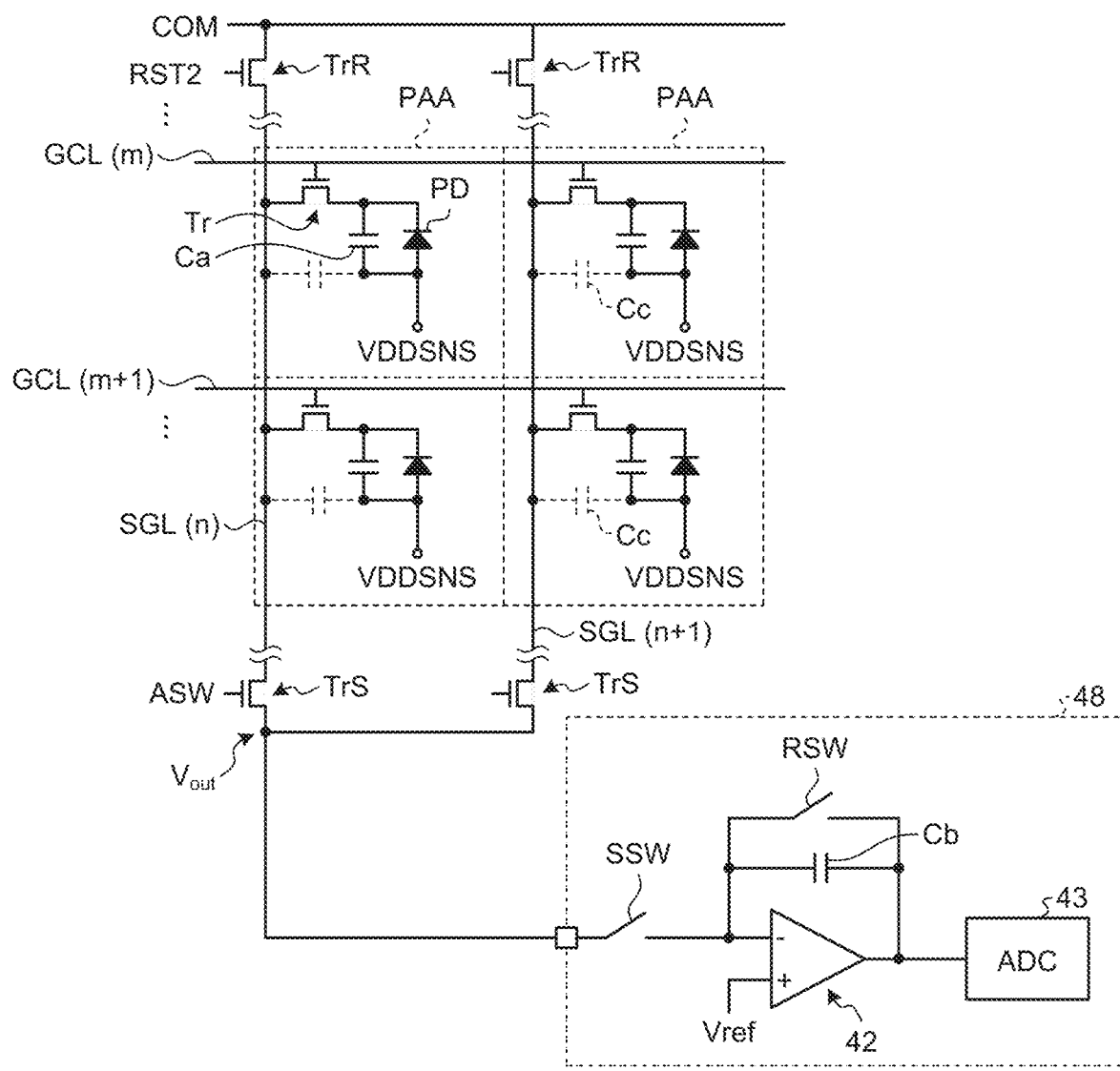
FIG. 4 is a circuit diagram illustrating a plurality of partial detection areas.

FIG. 4 is a circuit diagram illustrating the partial detection areas. FIG. 4 also illustrates a circuit configuration of the detection circuit 48. As illustrated in FIG. 4, each of the partial detection areas PAA includes the optical sensor PD, the capacitive element Ca, and a corresponding one of the first switching elements Tr. The capacitive element Ca is a capacitor (sensor capacitance) generated in the optical sensor PD and is equivalently coupled in parallel to the optical sensor PD. In addition, a signal line capacitor Cc is a parasitic capacitor (parasitic capacitance) generated in the signal line SGL and is equivalently generated between the signal line SGL and a node between the anode of the optical sensor PD and one end side of the capacitive element Ca.

FIG. 4 illustrates two gate lines GCL(m) and GCL(m+1) arranged in the second direction Dy among the gate lines GCL. FIG. 4 also illustrates two signal lines SGL(n) and SGL(n+1) arranged in the first direction Dx among the signal lines SGL. The partial detection area PAA is an area surrounded by the gate lines GCL and the signal lines SGL.

Each of the first switching elements Tr is provided correspondingly to the optical sensor PD. The first switching element Tr includes a thin-film transistor, and in this example, includes an n-channel metal oxide semiconductor (MOS) thin-film transistor (TFT).

The gates of the first switching elements Tr belonging to the partial detection areas PAA arranged in the first direction Dx are coupled to the gate line GCL. The sources of the first switching elements Tr belonging to the partial detection areas PAA arranged in the second direction Dy are coupled to the signal line SGL. The drain of the first switching element Tr is coupled to the cathode of the optical sensor PD and the capacitive element Ca.

The anode of the optical sensor PD is supplied with the sensor power supply signal VDDSNS from the power supply circuit 123. The signal line SGL and the capacitive element Ca are supplied with the reference signal COM that serves as an initial potential of the signal line SGL and the capacitive element Ca from the power supply circuit 123.

When the partial detection area PAA is irradiated with light, a current corresponding to the amount of the light flows through the optical sensor PD. As a result, an electric charge is stored in the capacitive element Ca. After the first switching element Tr is turned on, a current corresponding to the electric charge stored in the capacitive element Ca flows through the signal line SGL. The signal line SGL is coupled to the detection circuit 48 through a corresponding one of the third switching elements TrS of the signal line selection circuit 16. Thus, the detection device 1 can detect a signal corresponding to the amount of the light irradiating the optical sensor PD for each of the partial detection areas PAA or each block unit PAG.

During a reading period Pdet (refer to FIG. 6), a switch SSW of the detection circuit 48 is turned on, and the detection circuit 48 is coupled to the signal lines SGL. The detection signal amplifier 42 of the detection circuit 48 converts a current supplied from the signal line SGL into a voltage corresponding to the value of the current, and amplifies the result. A reference potential (Vref) having a fixed potential is supplied to a non-inverting input terminal (+) of the detection signal amplifier 42, and the signal lines SGL are coupled to an inverting input terminal (−) of the detection signal amplifier 42. In the present embodiment, the same signal as the reference signal COM is supplied as the reference potential (Vref). The detection signal amplifier 42 includes a capacitive element Cb and a reset switch RSW. During a reset period Prst (refer to FIG. 6), the reset switch RSW is turned on, and an electric charge of the capacitive element Cb is reset.

Figure 5A:
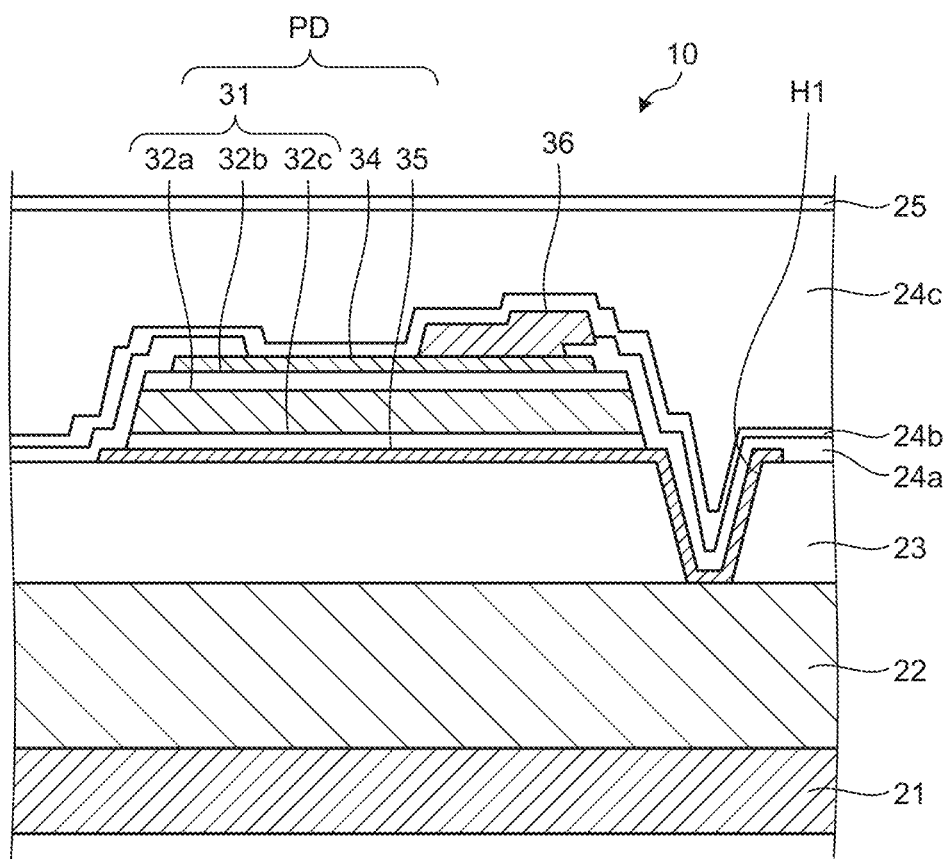
FIG. 5A is a sectional view illustrating a schematic sectional configuration of a sensor.

The following describes a configuration of the optical sensor PD. FIG. 5A is a sectional view illustrating a schematic sectional configuration of the sensor. As illustrated in FIG. 5A, the sensor 10 includes the sensor base member 21, a TFT layer 22, an insulating layer 23, the optical sensor PD, and insulating layers 24a, 24b, 24c, and 25. The sensor base member 21 is an insulating base member, and is made using, for example, glass or a resin material. The sensor base member 21 is not limited to having a flat plate shape, and may have a curved surface. In this case, the sensor base member 21 can be a film-like resin. The sensor base member 21 has a first surface and a second surface on the opposite side to the first surface. The TFT layer 22, the insulating layer 23, the optical sensor PD, and the insulating layers 24 and 25 are stacked in this order on the first surface.

The TFT layer 22 is provided with circuits such as the gate line drive circuit 15 and the signal line selection circuit 16 described above. The TFT layer 22 is also provided with TFTs, such as the first switching elements Tr, and various types of wiring such as the gate lines GCL and signal lines SGL. The sensor base member 21 and the TFT layer 22 serve as a drive circuit board that drives the sensing region for each predetermined detection area and are also called a backplane or an array substrate.

The insulating layer 23 is an organic insulating layer, and is provided on the TFT layer 22. The insulating layer 23 is a planarizing layer that planarizes asperities formed by the first switching elements Tr and various conductive layers formed in the TFT layer 22.

The optical sensor PD is provided on the insulating layer 23. The optical sensor PD includes a lower electrode 35, a semiconductor layer 31, and an upper electrode 34, which are stacked in this order.

The lower electrode 35 is provided on the insulating layer 23, and is electrically coupled to the first switching element Tr in the TFT layer 22 through a contact hole H1. The lower electrode 35 is the cathode of the optical sensor PD and is an electrode for reading the detection signal Vdet. A metal material such as molybdenum (Mo) or aluminum (Al) is used as the lower electrode 35. Alternatively, the lower electrode 35 may be a multilayered film formed by stacking these metal materials. The lower electrode 35 may be formed of, for example, a light-transmitting conductive material such as indium tin oxide (ITO).

The semiconductor layer 31 is formed of amorphous silicon (a-Si). The semiconductor layer 31 includes an i-type semiconductor layer 32a, a p-type semiconductor layer 32b, and an n-type semiconductor layer 32c. The i-type semiconductor layer 32a, the p-type semiconductor layer 32b, and the n-type semiconductor layer 32c constitute a specific example of a photoelectric conversion element. In FIG. 5A, the n-type semiconductor layer 32c, the i-type semiconductor layer 32a, and the p-type semiconductor layer 32b are stacked in this order in a direction orthogonal to a surface of the sensor base member 21. However, the semiconductor layer 31 may have a reversed configuration, that is, the p-type semiconductor layer 32b, the i-type semiconductor layer 32a, and the n-type semiconductor layer 32c may be stacked in this order. The semiconductor layer 31 may be a photoelectric conversion element formed of organic semiconductors.

The a-Si of the n-type semiconductor layer 32c is doped with impurities to form an n+ region. The a-Si of the p-type semiconductor layer 32b is doped with impurities to form a p+ region. The i-type semiconductor layer 32a is, for example, a non-doped intrinsic semiconductor, and has lower conductivity than that of the p-type semiconductor layer 32b and the n-type semiconductor layer 32c.

The upper electrode 34 is the anode of the optical sensor PD, and is an electrode for supplying the power supply signal VDDSNS to a photoelectric conversion layer. The upper electrode 34 is a light-transmitting conductive layer of, for example, ITO, and a plurality of the upper electrodes 34 are provided for each of the optical sensors PD.

The insulating layers 24a and 24b are provided on the insulating layer 23. The insulating layer 24a covers the periphery of the upper electrode 34, and is provided with an opening in a position overlapping the upper electrode 34. Coupling wiring 36 is coupled to the upper electrode 34 at a portion of the upper electrode 34 not provided with the insulating layer 24a. The insulating layer 24b is provided on the insulating layer 24a so as to cover the upper electrode 34 and the coupling wiring 36. The insulating layer 24c serving as a planarizing layer is provided on the insulating layer 24b. The insulating layer 25 is provided on the insulating layer 24c. However, the insulating layer 25 need not be provided.

Figure 5B:
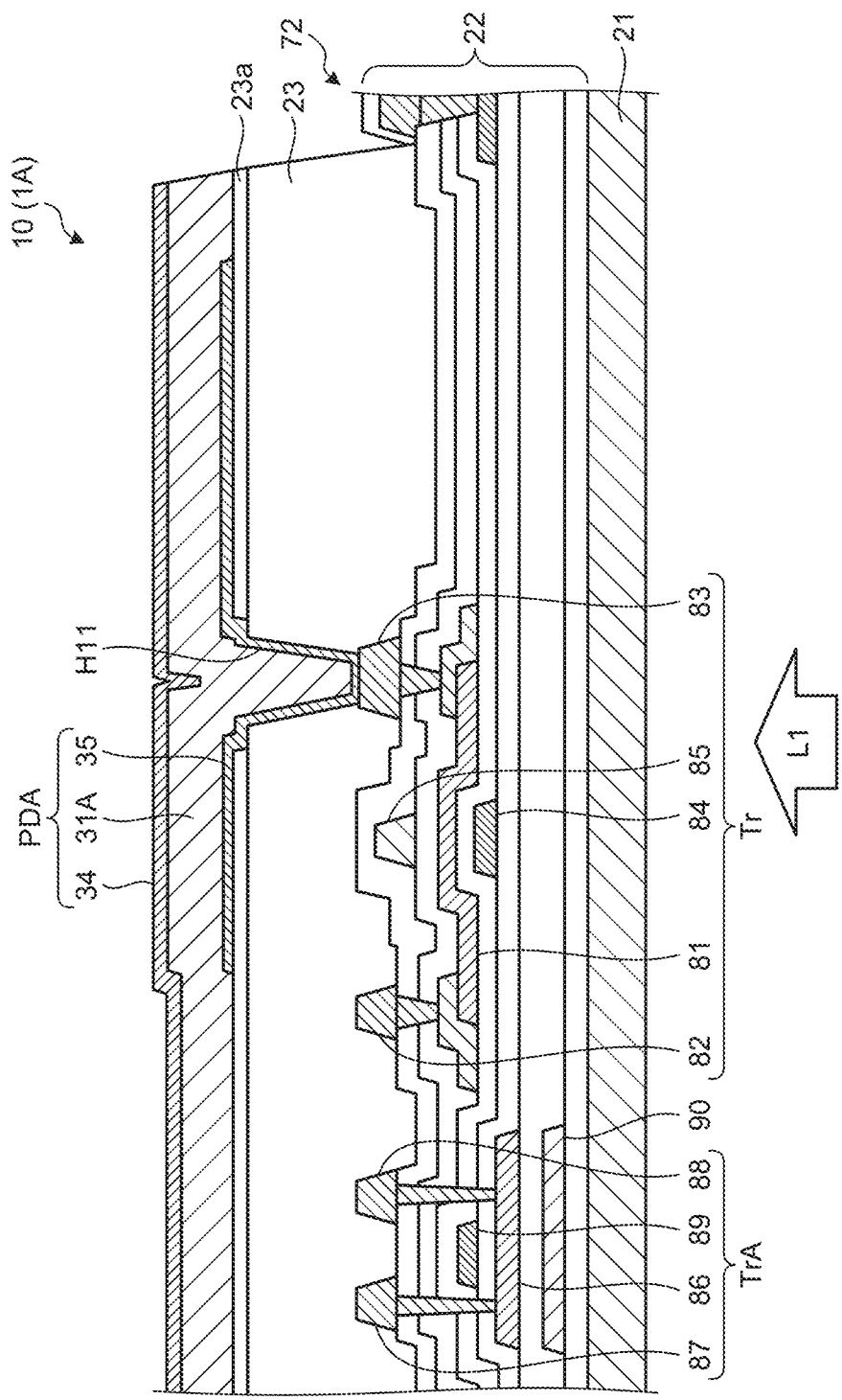
FIG. 5B is a sectional view illustrating a schematic sectional configuration of the sensor of a detection device according to a first modification.

FIG. 5B is a sectional view illustrating a schematic sectional configuration of the sensor of a detection device according to a first modification. As illustrated in FIG. 5B, in a detection device 1A of the first modification, an optical sensor PDA is provided above an insulating layer 23a. The insulating layer 23a is an inorganic insulating layer provided so as to cover the insulating layer 23, and is formed of, for example, silicon nitride (SiN). The optical sensor PDA includes a photoelectric conversion layer 31A, the lower electrode 35 (cathode electrode), and the upper electrode 34 (anode electrode). The lower electrode 35, the photoelectric conversion layer 31A, and the upper electrode 34 are stacked in this order in a direction orthogonal to a first surface S1 of the sensor base member 21.

The photoelectric conversion layer 31A changes in characteristics (for example, voltage-current characteristics and a resistance value) depending on light emitted thereto. An organic material is used as a material of the photoelectric conversion layer 31A. Specifically, as the photoelectric conversion layer 31A, low-molecular-weight organic materials can be used including, for example, fullerene ($C_{60}$), phenyl-$C_{61}$-butyric acid methyl ester (PCBM), copper phthalocyanine (CuPc), fluorinated copper phthalocyanine ($F_{16}$CuPc), 5,6,11,12-tetraphenyltetracene (rubrene), and perylene diimide (PDI) (a derivative of perylene).

The photoelectric conversion layer 31A can be formed by a vapor deposition process (dry process) using the above-listed low-molecular-weight organic materials. In this case, the photoelectric conversion layer 31A may be, for example, a multilayered film of CuPc and $F_{16}$CuPc, or a multilayered film of rubrene and $C_{60}$. The photoelectric conversion layer 31A can also be formed by a coating process (wet process). In this case, the photoelectric conversion layer 31A is made using a material obtained by combining the above-listed low-molecular-weight organic materials with high-molecular-weight organic materials. As the high-molecular-weight organic materials, for example, poly(3-hexylthiophene) (P3HT) and F8-alt-benzothiadiazole (F8BT) can be used. The photoelectric conversion layer 31A can be a film in the state of a mixture of P3HT and PCBM or a film in the state of a mixture of F8BT and PDI.

The lower electrode 35 faces the upper electrode 34 with the photoelectric conversion layer 31A interposed therebetween. The upper electrode 34 is formed of, for example, a light-transmitting conductive material such as ITO. For example, a metal material such as silver (Ag) or aluminum (Al) is used as the lower electrode 35. Alternatively, the lower electrode 35 may be made of an alloy material containing at least one or more of these metal materials.

The lower electrode 35 can be formed as a light-transmitting transflective electrode by controlling the film thickness of the lower electrode 35. For example, the lower electrode 35 is formed of a thin Ag film having a thickness of 10 nm so as to have light transmittance of approximately 60%. In this case, the optical sensor PDA can detect light emitted from both sides of the sensor base member 21, for example, both light L1 emitted from the first surface S1 side and light emitted from a second surface S2 side.

Although not illustrated in FIG. 5B, the insulating layers 24a and 24b (protective films) may be provided so as to cover the upper electrode 34. The protective film is a passivation film and is provided to protect the optical sensor PDA.

As illustrated in FIG. 5B, the TFT layer 22 is provided with the first switching element Tr electrically coupled to the optical sensor PDA. The first switching element Tr includes a semiconductor layer 81, a source electrode 82, a drain electrode 83, and gate electrodes 84 and 85. The lower electrode 35 of the optical sensor PDA is electrically coupled to the drain electrode 83 of the first switching element Tr through a contact hole H11 provided in the insulating layers 23 and 23a.

The first switching element Tr has what is called a dual-gate structure provided with the gate electrodes 84 and 85 on the upper and lower sides of the semiconductor layer 81. However, the first switching element Tr is not limited to this structure and may have a top-gate structure or a bottom-gate structure.

FIG. 5B schematically illustrates a second switching element TrA and a terminal 72 provided in the peripheral area GA. The second switching element TrA is, for example, a switching element provided in the gate line drive circuit 15 (refer to FIG. 1). The second switching element TrA includes a semiconductor layer 86, a source electrode 87, a drain electrode 88, and a gate electrode 89. The second switching element TrA has what is called a top-gate structure provided with the gate electrode 89 on the upper side of the semiconductor layer 86. A light-blocking layer 90 is provided between the semiconductor layer 86 and the sensor base member 21 on the lower side of the semiconductor layer 86. The second switching element TrA is, however, not limited to the above-described structure and may have a bottom-gate structure or a dual-gate structure.

The semiconductor layer 81 of the first switching element Tr is provided in a layer different from that of the semiconductor layer 86 of the second switching element TrA. The semiconductor layer 81 of the first switching element Tr is formed of, for example, an oxide semiconductor. The semiconductor layer 86 of the second switching element TrA is formed of, for example, polysilicon.

Figure 6:
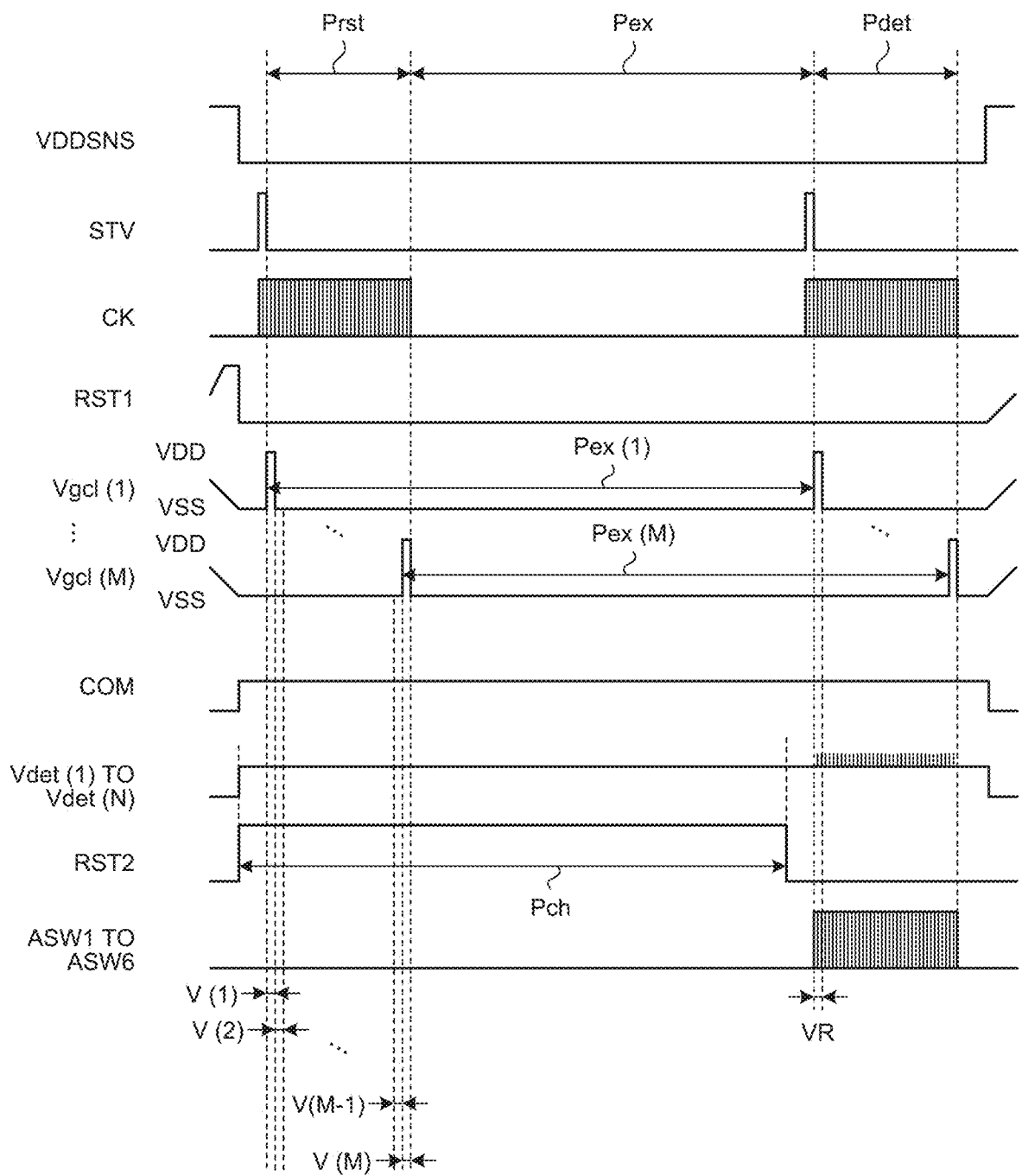
FIG. 6 is a timing waveform diagram illustrating an operation example of a detection device of a comparative example.
Figure 7:
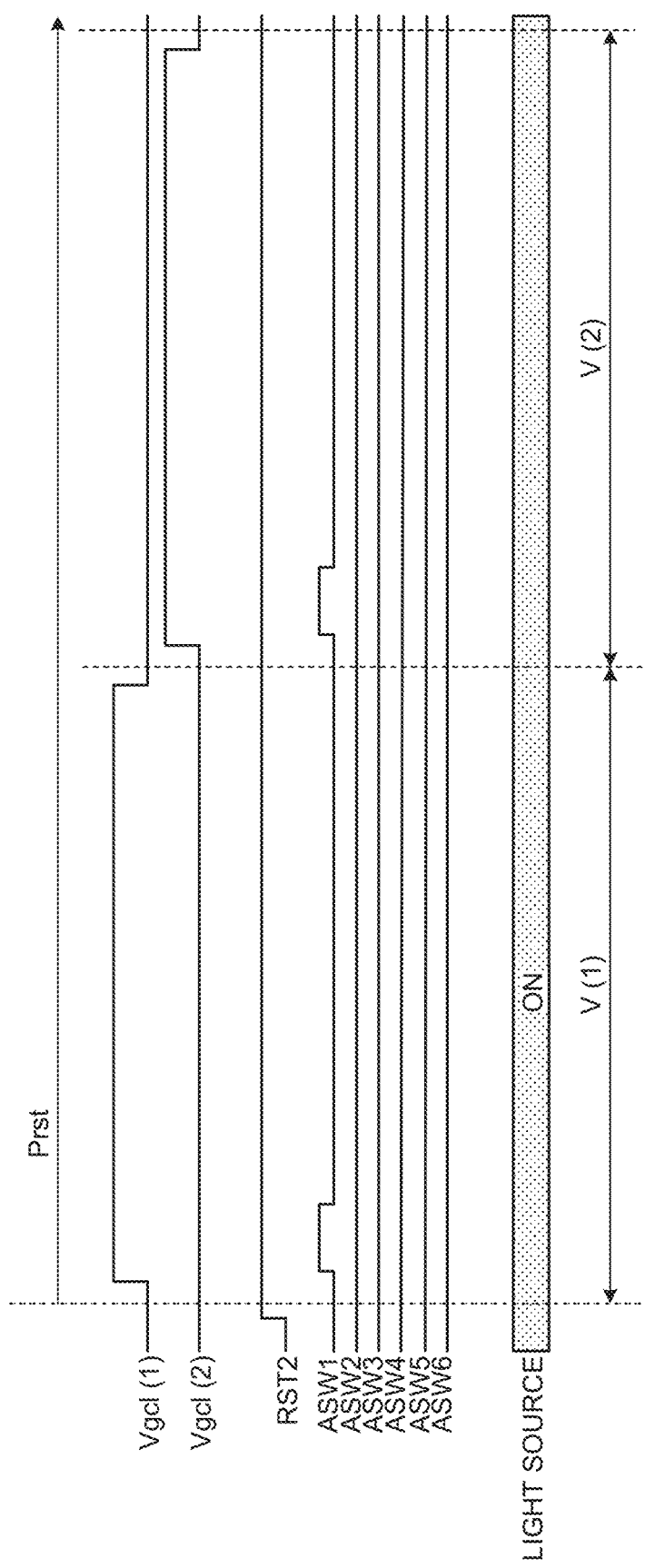
FIG. 7 is a timing waveform diagram illustrating an operation example during a reset period in FIG. 6.
Figure 8:
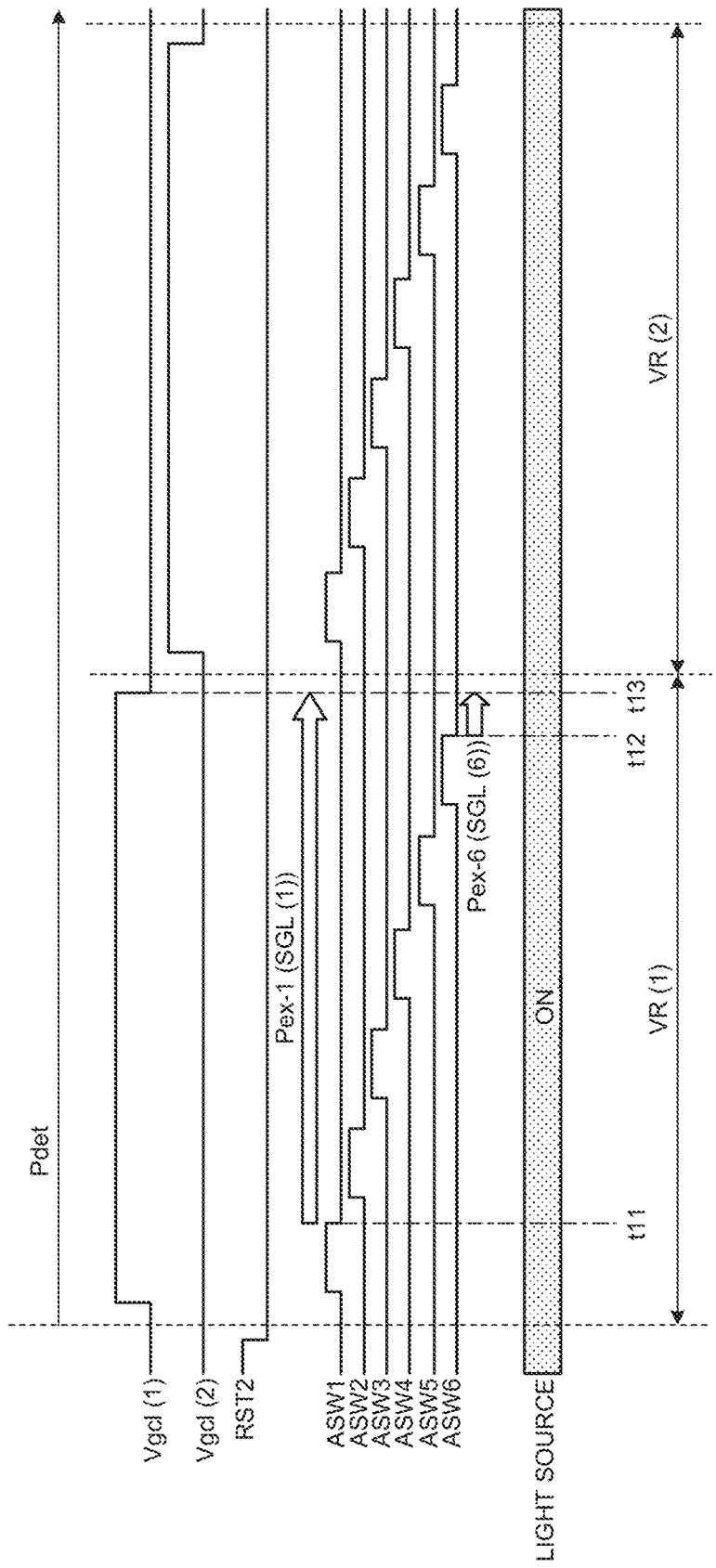
FIG. 8 is a timing waveform diagram illustrating an operation example during a reading period in FIG. 6.
Figure 9:
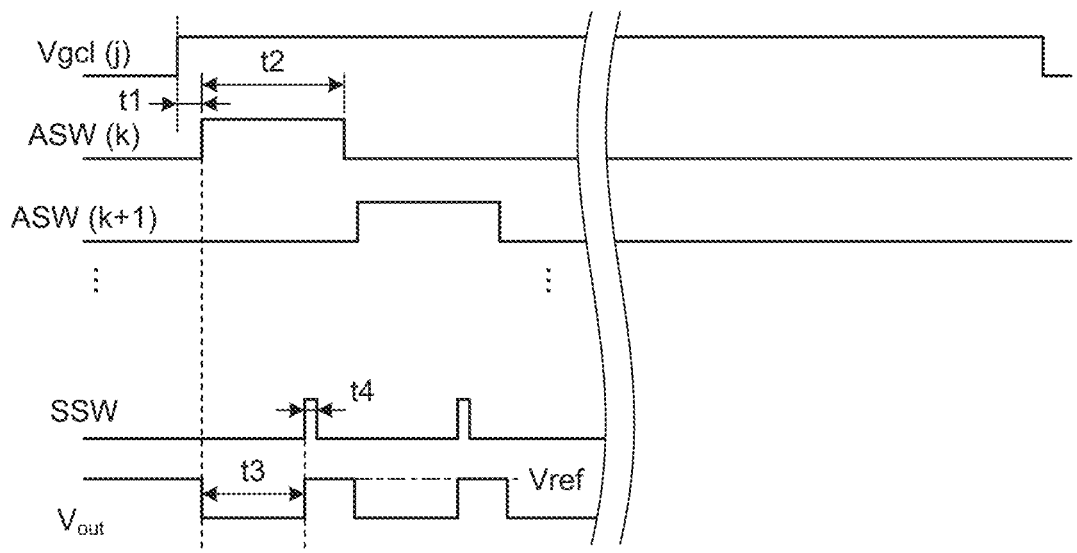
FIG. 9 is a timing waveform diagram illustrating an operation example during a drive period of one gate line included in the reading period in FIG. 6.
Figure 10:
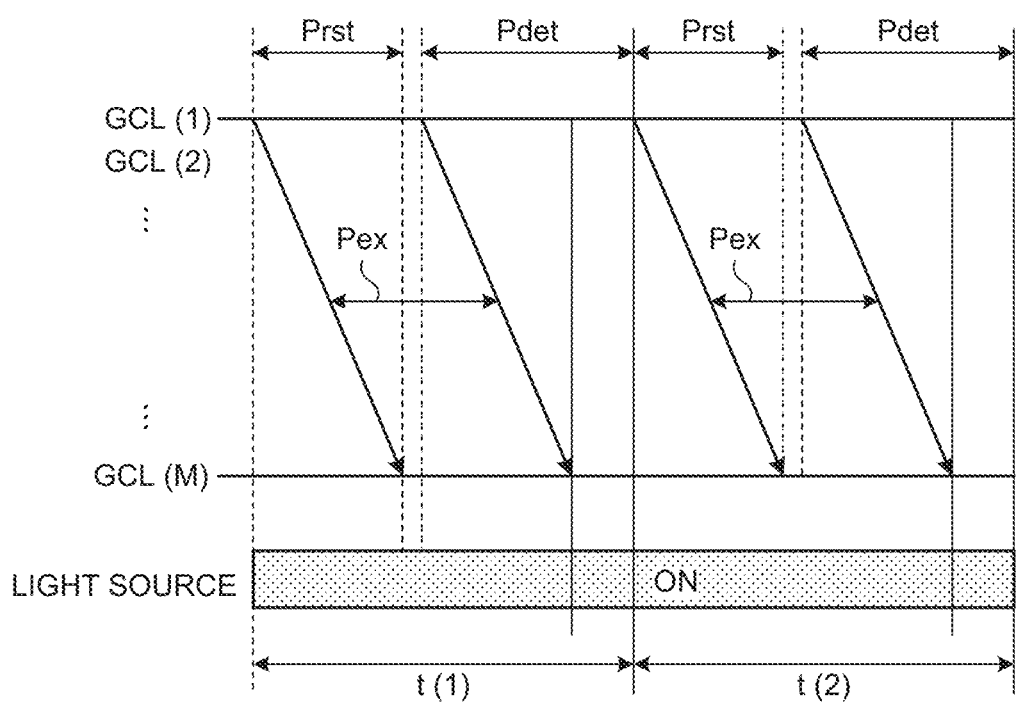
FIG. 10 is an explanatory diagram for explaining a relation between driving of the sensor of the detection device of the comparative example and a lighting operation of light sources thereof.

In order to facilitate understanding of an operation example of the detection device 1 of the present embodiment, the following describes an operation example of a detection device of a comparative example. FIG. 6 is a timing waveform diagram illustrating an operation example of the detection device of the comparative example. FIG. 7 is a timing waveform diagram illustrating an operation example during the reset period in FIG. 6. FIG. 8 is a timing waveform diagram illustrating an operation example during the reading period in FIG. 6. FIG. 9 is a timing waveform diagram illustrating an operation example during a drive period of one gate line included in a row reading period VR in FIG. 6. FIG. 10 is an explanatory diagram for explaining a relation between driving of the sensor of the detection device of the comparative example and a lighting operation of the light sources thereof.

As illustrated in FIG. 6, the detection device of the comparative example has the reset period Prst, an exposure period Pex, and the reading period Pdet. The power supply circuit 123 supplies the sensor power supply signal VDDSNS to the anode of the optical sensor PD over the reset period Prst, the exposure period Pex, and the reading period Pdet. The sensor power supply signal VDDSNS is a signal for applying a reverse bias between the anode and the cathode of the optical sensor PD. For example, the reference signal COM of substantially 0.75 V is applied to the cathode of the optical sensor PD, and the sensor power supply signal VDDSNS of substantially −1.25 V is applied to the anode thereof. As a result, a reverse bias of substantially 2.0 V is applied between the anode and the cathode. The control circuit 122 sets the reset signal RST2 to "H", and then, supplies the start signal STV and the clock signal CK to the gate line drive circuit 15 to start the reset period Prst. During the reset period Prst, the control circuit 122 supplies the reference signal COM to the reset circuit 17, and uses the reset signal RST2 to turn on the fourth switching elements TrR for supplying a reset voltage. This operation supplies the reference signal COM as the reset voltage to each of the signal lines SGL. The reference signal COM is set to, for example, 0.75 V.

During the reset period Prst, the gate line drive circuit 15 sequentially selects each of the gate lines GCL based on the start signal STV, the clock signal CK, and the reset signal RST1. The gate line drive circuit 15 sequentially supplies the gate drive signals Vgcl {Vgcl(1), . . . , Vgcl(M)} to the gate lines GCL. The gate drive signal Vgcl has a pulsed waveform having a power supply voltage VDD serving as a high-level voltage and a power supply voltage VSS serving as a low-level voltage. In FIG. 6, M gate lines GCL (where M is, for example, 256) are provided, and the gate drive signals Vgcl(1), . . . , Vgcl(M) are sequentially supplied to the respective gate lines GCL. Thus, the first switching elements Tr are sequentially brought into a conducting state and supplied with the reset voltage on a row-by-row basis. For example, a voltage of 0.75 V of the reference signal COM is supplied as the reset voltage.

Specifically, as illustrated in FIG. 7, the gate line drive circuit 15 supplies the gate drive signal Vgcl(1) at the high-level voltage (power supply voltage VDD) to the gate line GCL(1) during a period V(1). The control circuit 122 supplies any one of selection signals ASW1, . . . , ASW6 (selection signal ASW1 in FIG. 7) to the signal line selection circuit 16 during a period in which the gate drive signal Vgcl(1) is at the high-level voltage (power supply voltage VDD). This operation couples the signal line SGL of the partial detection area PAA selected by the gate drive signal Vgcl(1) to the detection circuit 48. As a result, the reset voltage (reference signal COM) is also supplied to coupling wiring between the third switching element TrS and the detection circuit 48.

In the same manner, the gate line drive circuit 15 supplies the gate drive signals Vgcl(2), . . . , Vgcl(M−1), Vgcl(M) at the high-level voltage to gate lines GCL(2), . . . , GCL(M−1), GCL(M) during periods V(2), . . . , V(M−1), V(M), respectively.

Thus, during the reset period Prst, the capacitive elements Ca of all the partial detection areas PAA are sequentially electrically coupled to the signal lines SGL, and are supplied with the reference signal COM. As a result, the capacitance of the capacitive elements Ca is reset. The capacitance of the capacitive elements Ca of some of the partial detection areas PAA can be reset by partially selecting the gate lines and the signal lines SGL.

Examples of the exposure timing control method include a control method of exposure during non-selection of gate lines and a full-time control method of exposure. In the control method of exposure during non-selection of gate lines, the gate drive signals {Vgcl(1), . . . , Vgcl(M)} are sequentially supplied to all the gate lines GCL coupled to the optical sensors PD serving as the detection targets, and all the optical sensors PD serving as the detection targets are supplied with the reset voltage. Then, after all the gate lines GCL coupled to the optical sensors PD serving as the detection targets are set to a low voltage (the first switching elements Tr are turned off), the exposure starts and the exposure is performed during the exposure period Pex. After the exposure ends, the gate drive signals {Vgcl(1), . . . , Vgcl(M)} are sequentially supplied to the gate lines GCL coupled to the optical sensors PD serving as the detection targets as described above, and reading is performed during the reading period Pdet. In the full-time control method of exposure, control for performing the exposure can also be performed during the reset period Prst and the reading period Pdet (full-time exposure control). In this case, the exposure period Pex(1) starts after the gate drive signal Vgcl(1) is supplied to the gate line GCL during the reset period Prst. The term "exposure periods Pex{(1), . . . , (M)}" refers to periods during which the capacitive elements Ca are charged from the optical sensors PD. The electric charge stored in the capacitive element Ca during the reset period Prst causes a reverse directional current (from cathode to anode) to flow through the optical sensor PD due to light irradiation, and the potential difference in the capacitive element Ca decreases. The start timing and the end timing of the actual exposure periods Pex(1), . . . , Pex(M) are different among the partial detection areas PAA corresponding to the gate lines GCL. The "actual exposure period" is not a period during which the light source emits light but a period during which the electric charges corresponding to the light received by the optical sensors PD are stored in the respective capacitive elements Ca in the lighting period of the light source. Each of the exposure periods Pex(1), . . . , Pex(M) starts when the gate drive signal Vgcl changes from the power supply voltage VDD serving as the high-level voltage to the power supply voltage VSS serving as the low-level voltage during the reset period Prst. Each of the exposure periods Pex(1), . . . , Pex(M) ends when the gate drive signal Vgcl changes from the power supply voltage VSS to the power supply voltage VDD during the reading period Pdet. The lengths of the exposure time of the exposure periods Pex(1), . . . , Pex(M) are equal.

In the control method of exposure during non-selection of gate lines, a current corresponding to the light irradiating the optical sensor PD flows in the optical sensor PD in each of the partial detection areas PAA during the exposure periods Pex {(1) . . . (M)}. As a result, an electric charge is stored in each of the capacitive elements Ca.

At a time before the reading period Pdet starts, the control circuit 122 sets the reset signal RST2 to a low-level voltage. This operation stops operation of the reset circuit 17. The reset signal may be set to a high-level voltage only during the reset period Prst. During the reading period Pdet, the gate line drive circuit 15 sequentially supplies the gate drive signals Vgcl(1) . . . , Vgcl(M) to the gate lines GCL in the same manner as during the reset period Prst.

Specifically, as illustrated in FIG. 8, the gate line drive circuit 15 supplies the gate drive signal Vgcl(1) at the high-level voltage (power supply voltage VDD) to the gate line GCL(1) during a row reading period VR(1). The control circuit 122 sequentially supplies selection signals ASW1, . . . , ASW6 to the signal line selection circuit 16 during the period in which the gate drive signal Vgcl(1) is at the high-level voltage (power supply voltage VDD). This operation sequentially or simultaneously couples the signal lines SGL of the partial detection areas PAA selected by the gate drive signal Vgcl(1) to the detection circuit 48. As a result, the detection signal Vdet for each of the partial detection areas PAA is supplied to the detection circuit 48.

In the same manner, the gate line drive circuit 15 supplies the gate drive signals Vgcl(2), . . . , Vgcl(M−1), Vgcl(M) at the high-level voltage to the gate lines GCL(2), . . . , GCL(M−1), GCL(M) during row reading periods VR(2), . . . , VR(M−1), VR(M), respectively. That is, the gate line drive circuit 15 supplies the gate drive signal Vgcl to the gate line GCL during each of the row reading periods VR(1), VR(2), . . . , VR(M−1), VR(M). The signal line selection circuit 16 sequentially selects each of the signal lines SGL based on the selection signal ASW in each period in which the gate drive signal Vgcl is set to the high-level voltage. The signal line selection circuit 16 sequentially couples each of the signal lines SGL to one detection circuit 48. Thus, the detection device 1 can output the detection signals Vdet of all the partial detection areas PAA to the detection circuit 48 during the reading period Pdet.

With reference to FIG. 9, the following describes the operation example during the row reading period VR that is a supply period of one of the gate drive signals Vgcl(j) in FIG. 6. In FIG. 6, the reference sign of the row reading period VR is assigned to the first gate drive signal Vgcl(1). The same applies to the other gate drive signals Vgcl(2) . . . , Vgcl(M). The index j is any one of the natural numbers 1 to M.

As illustrated in FIGS. 9 and 4, an output ($V_{out}$) of each of the third switching elements TrS has been reset to the reference potential (Vref) voltage in advance. The reference potential (Vref) serves as the reset voltage, and is set to, for example, 0.75 V. Then, the gate drive signal Vgcl(j) is set to a high level, and the first switching elements Tr of a corresponding row are turned on. Thus, each of the signal lines SGL in each row is set to a voltage corresponding to the electric charge stored in the capacitor (capacitive element Ca) of the partial detection area PAA. After a period t1 elapses from a rising edge of the gate drive signal Vgcl(j), a period t2 starts in which the selection signal ASW(k) is set to a high level. After the selection signal ASW(k) is set to the high level and the third switching element TrS is turned on, the electric charge stored in the capacitor (capacitive element Ca) of the partial detection area PAA coupled to the detection circuit 48 through the third switching element TrS changes the output ($V_{out}$) of the third switching element TrS (refer to FIG. 4) to a voltage corresponding to the electric charge stored in the capacitor (capacitive element Ca) of the partial detection area PAA (in a period t3). In the example of FIG. 9, this voltage is lower than the reset voltage as illustrated in the period t3. Then, after the switch SSW is turned on (period t4 during which an SSW signal is set to a high level), the electric charge stored in the capacitor (capacitive element Ca) of the partial detection area PAA moves to the capacitor (capacitive element Cb) of the detection signal amplifier 42 of the detection circuit 48, and the output voltage of the detection signal amplifier 42 is set to a voltage corresponding to the electric charge stored in the capacitive element Cb. At this time, the potential of the inverting input portion of the detection signal amplifier 42 is set to an imaginary short-circuit potential of an operational amplifier, and therefore, becomes the reference potential (Vref). The A/D converter 43 reads the output voltage of the detection signal amplifier 42. In the example of FIG. 9, waveforms of the selection signals ASW(k), ASW(k+1), . . . corresponding to the signal lines SGL of the respective columns are set to a high level to sequentially turn on the third switching elements TrS, and the same operation is sequentially performed. This operation sequentially reads the electric charges stored in the capacitors (capacitive elements Ca) of the partial detection areas PAA coupled to the gate line GCL. ASW(k), ASW(k+1), . . . in FIG. 9 are, for example, any of ASW1 to ASW6 in FIG. 8.

Specifically, after the period t4 starts in which the switch SSW is on, the electric charge moves from the capacitor (capacitive element Ca) of the partial detection area PAA to the capacitor (capacitive element Cb) of the detection signal amplifier 42 of the detection circuit 48. At this time, the non-inverting input (+) of the detection signal amplifier 42 is set to the reference potential (Vref) voltage (for example, 0.75 V). As a result, the output ($V_{out}$) of the third switching element TrS is also set to the reference potential (Vref) voltage due to the imaginary short-circuit between input ends of the detection signal amplifier 42. The voltage of the capacitive element Cb is set to a voltage corresponding to the electric charge stored in the capacitor (capacitive element Ca) of the partial detection area PAA at a location where the third switching element TrS is turned on in response to the selection signal ASW(k). After the output ($V_{out}$) of the third switching element TrS is set to the reference potential (Vref) voltage due to the imaginary short-circuit, the output of the detection signal amplifier 42 reaches a voltage corresponding to the capacitance of the capacitive element Cb, and this output voltage is read by the A/D converter 43. The voltage of the capacitive element Cb is, for example, a voltage between two electrodes provided on a capacitor constituting the capacitive element Cb.

The period t1 is, for example, 20 µs. The period t2 is, for example, 60 µs. The period t3 is, for example, 44.7 µs. The period t4 is, for example, 0.98 µs.

As illustrated in FIG. 10, in each of a period t(1) and a period t(2), the detection device 1 performs the processing in the reset period Prst, the processing in the exposure periods Pex{(1), . . . , (M)}, and the processing in the reading period Pdet described above. In the reset period Prst and the reading period Pdet, the gate line drive circuit 15 sequentially scans the gate lines GCL(1) to GCL(M). In the following description, "one frame detection" denotes detection operation of one frame, that is, the detection in each period t. More specifically, "one frame detection" denotes the detection for acquiring the detection signals Vdet from the signal lines SGL in the respective columns by scanning the gate lines GCL(1) to GCL(M) in the reset period Prst and the reading period Pdet.

The light sources (first light sources 61 or second light sources 62) are continuously turned on during the periods t(1) and t(2). The control circuit 122 can control the lighting and the non-lighting of the light sources depending on the detection target. For example, the control circuit 122 may alternately switch between on and off of the first and the second light sources 61 and 62 at intervals of a period of time, or may continuously turn on either the first light source 61 or the second light source 62.

Although FIGS. 6 to 10 illustrate the example in which the gate line drive circuit 15 individually selects the gate line GCL, the present disclosure is not limited to this example. The gate line drive circuit 15 may simultaneously select a predetermined number (two or more) of the gate lines GCL, and sequentially supply the gate drive signals Vgcl to the gate lines GCL in units of the predetermined number of the gate lines GCL. The signal line selection circuit 16 may also simultaneously couple a predetermined number (two or more) of the signal lines SGL to one detection circuit 48. Moreover, the gate line drive circuit 15 may skip some of the gate lines GCL and scan the remaining ones.

In the comparative example, as illustrated in FIG. 8, in the row reading period VR(1), the selection signals ASW1, . . . , ASW6 are sequentially supplied to the signal line selection circuit 16 during the period in which the gate drive signal Vgcl(1) is at the high-level voltage (power supply voltage VDD). That is, even after the selection signal ASW1 is set to a low-level voltage at time t11, the exposure continues during an exposure period Pex-1 until the gate drive signal Vgcl(1) is set to the low-level voltage at time t13. An electric charge corresponding to the exposure period Pex-1 is charged from the optical sensor PD to the signal line SGL(1) corresponding to the selection signal ASW1.

In the same manner, an electric charge is charged to each of the signal lines SGL in a corresponding one of exposure periods Pex-1, . . . , Pex-6 corresponding to the selection signals ASW1, . . . , ASW6. For example, the exposure period Pex-6 is a period after the selection signal ASW6 is set to the low-level voltage at time t12 until the gate drive signal Vgcl(1) is set to the low-level voltage at time t13. The exposure period Pex differs column by column.

In the next row reading period VR(2), the detection circuit 48 is supplied with a signal obtained by adding an electric charge that has been charged in the exposure periods Pex-1(SGL(1)), . . . , Pex-6(SGL(6)) of the previous row reading period VR(1) to the detection signal Vdet of the second row. Thus, the detection signal Vdet in each of the row reading periods VR changes depending on the detection results of the previous row reading period VR, which may reduce the detection accuracy.

Figure 11:
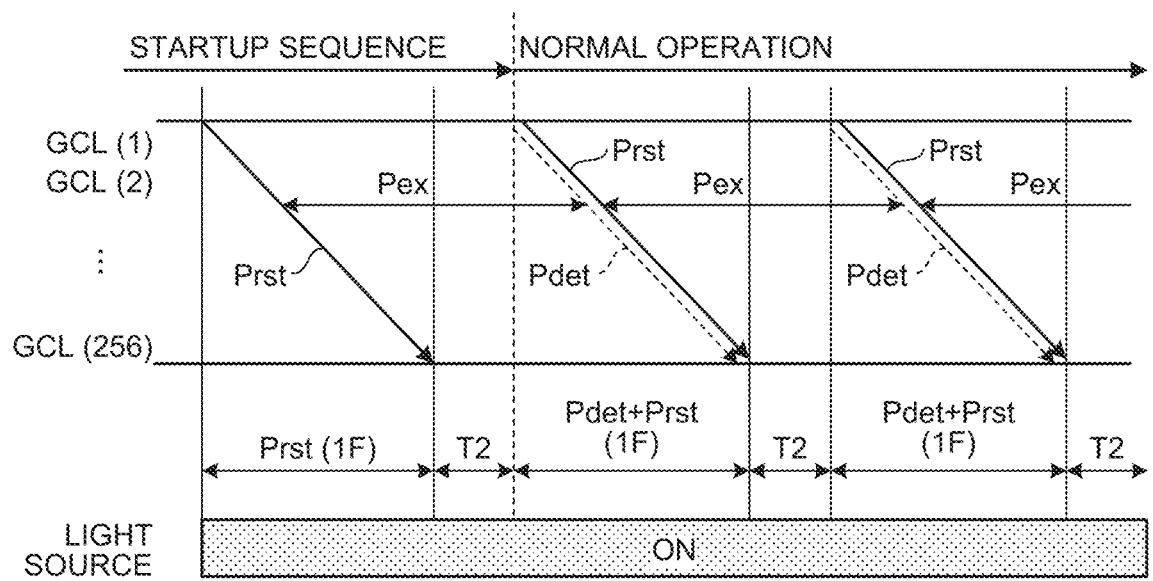
FIG. 11 is an explanatory diagram for explaining an operation example of the detection device according to the first embodiment.
Figure 12:
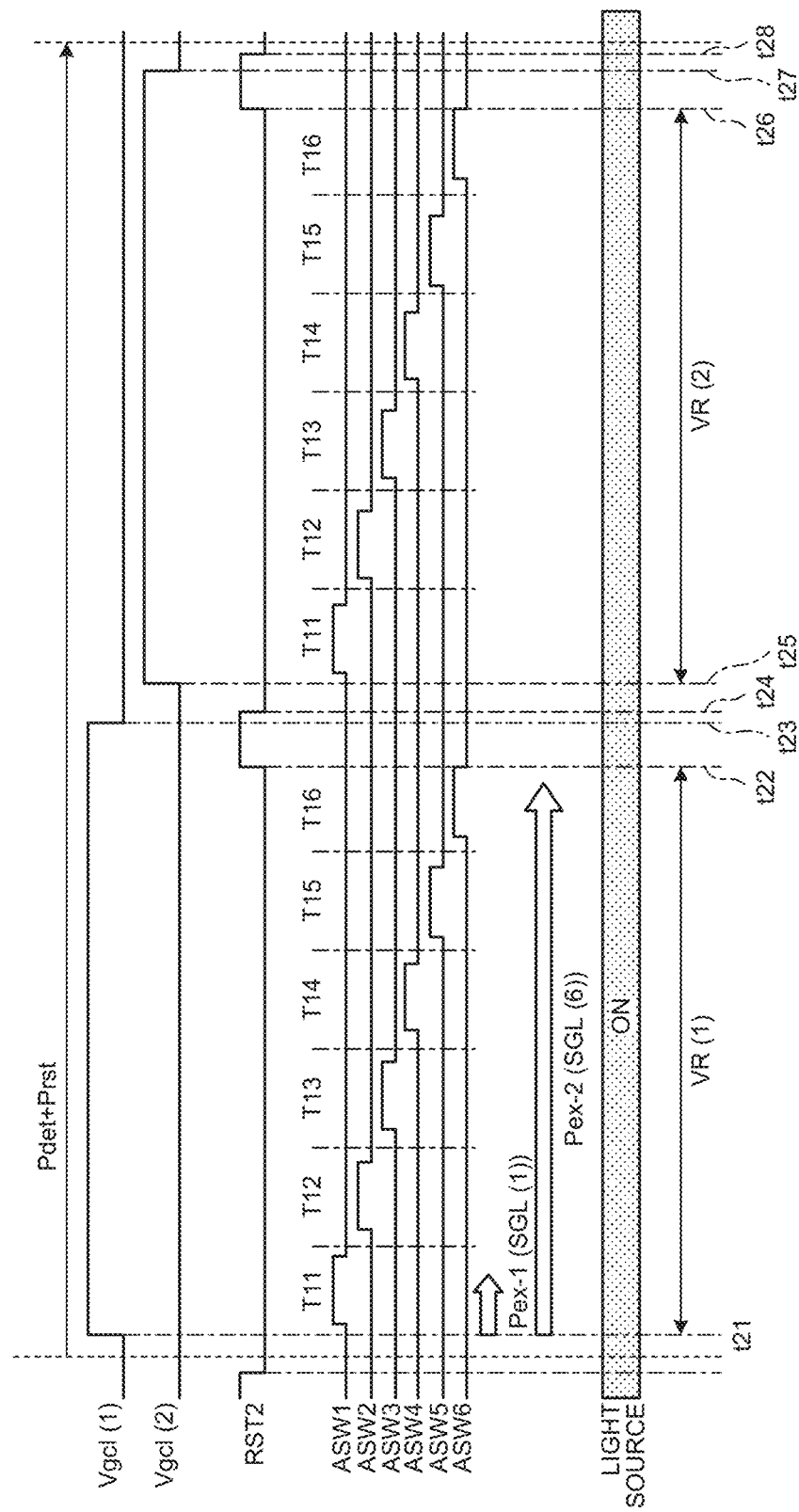
FIG. 12 is a timing waveform diagram illustrating the operation example of the detection device according to the first embodiment.

FIG. 11 is an explanatory diagram for explaining an operation example of the detection device according to the first embodiment. FIG. 12 is a timing waveform diagram illustrating the operation example of the detection device according to the first embodiment. In the comparative example, the processing of the reading period Pdet of one frame is executed after the processing of the reset period Prst of one frame in the one frame detection. In contrast, in the detection device 1 according to the first embodiment, as illustrated in FIG. 11, the processing of the reading period Pdet of one frame (1F) and the processing of the reset period Prst of one frame (1F) are executed in parallel.

In the present embodiment, the gate drive signal Vgcl is supplied to the gate lines GCL row by row, and the first switching elements Tr belonging to a predetermined row are brought into a coupled state. Specifically, as illustrated in FIG. 12, the gate line drive circuit 15 supplies the gate drive signal Vgcl(1) at the high-level voltage (power supply voltage VDD) to the gate line GCL(1) at time t21. The row reading period VR(1) starts at time t21 when the gate drive signal Vgcl(1) is set to the high-level voltage.

Specifically, the control circuit 122 sequentially supplies the selection signals ASW1, . . . , ASW6 to the signal line selection circuit 16 during the period in which the gate drive signal Vgcl(1) is at the high-level voltage (power supply voltage VDD). The third switching elements TrS are sequentially brought into the coupled state according to the selection signals ASW1, . . . , ASW6. That is, during the period of reading each row (row reading period VR(1)), the first switching elements Tr of the predetermined row are in the coupled state, and the signal line selection circuit 16 couples the signal lines SGL to the detection circuit 48 column by column in a predetermined order. As a result, the detection signal Vdet for each of the partial detection areas PAA is supplied to the detection circuit 48.

In FIG. 12, the selection signals ASW1, . . . , ASW6 are supplied in the order of periods T11, . . . , T16 in a time-division manner. At time t22, the control circuit 122 sets the selection signal ASW6 to the low-level voltage, and the reading of the last column ends. That is, in the present embodiment, the row reading period VR(1) ends when the gate drive signal Vgcl(1) is at the high-level voltage and the selection signal ASW6 changes to the low-level voltage.

After the completion of the reading period of a predetermined row (row reading period VR(1)) and before the start of the reading period of a row next to the predetermined row (row reading period VR(2)), a reset potential (reference signal COM) is supplied to the optical sensors PD and the signal lines SGL belonging to the predetermined row. Specifically, the control circuit 122 supplies the reset signal RST2 to the reset signal line Lrst at time t22. This operation turns on the fourth switching elements TrR to supply the reference signal COM to the optical sensors PD and the signal lines SGL corresponding to the gate line GCL(1).

In FIG. 12, the time when the reset signal RST2 is set to the high-level voltage coincides with the time when the selection signal ASW6 is set to the low-level voltage; both of them are at time t22. However, the timing is not limited thereto. The reset signal RST2 may be set to the high-level voltage after a predetermined period of time has elapsed since the selection signal ASW6 has been set to the low-level voltage.

Then, at time t23, the gate line drive circuit 15 sets the gate drive signal Vgcl(1) to the low-level voltage. This operation brings the first switching elements Tr of the predetermined row into a non-coupled state. At time t24, the control circuit 122 sets the reset signal RST2 to the low-level voltage. With this operation, the reading period Pdet and reset period Prst of the first row end.

Then, at time t25, the gate line drive circuit 15 supplies the gate drive signal Vgcl(2) at the high-level voltage (power supply voltage VDD) to the gate line GCL(2) of the second row. Subsequently, in the same manner as in the first row, the processing of the reading period Pdet and the processing of the reset period Prst of the second row are executed from time t26 to time t28. The one frame detection can be performed by repeating this scanning operation to the last row (gate line GCL(256)).

In the present embodiment, the reset period Prst is provided in each of the row reading periods VR. Therefore, even if the signal line SGL is charged with an electric charge after a predetermined column (for example, SGL(1)) is read, the charge is reset before the row reading period VR for the next row. Therefore, the detection device 1 can reduce variations in the detection signal Vdet that would be caused by the detection results in the previous row, and thus can increase the detection accuracy.

In the present embodiment, the reset potential is supplied after the row reading period VR for each row. Therefore, the reset period Prst is preferably provided as a startup sequence at the start of the detection device 1, as illustrated in FIG. 11. In the start-up sequence, no readout is performed and reset is performed by supplying a reset potential to the optical sensors PD and the signal lines SGL for one frame (1F). This operation can reduce the detection variations in the first reading period Pdet after the startup. The startup sequence is performed at the time of startup when the power of the detection device 1 is turned on, or when the detection device 1 returns from the sleep mode in which the detection device 1 does not perform the detection for a predetermined period of time.

Figure 13:
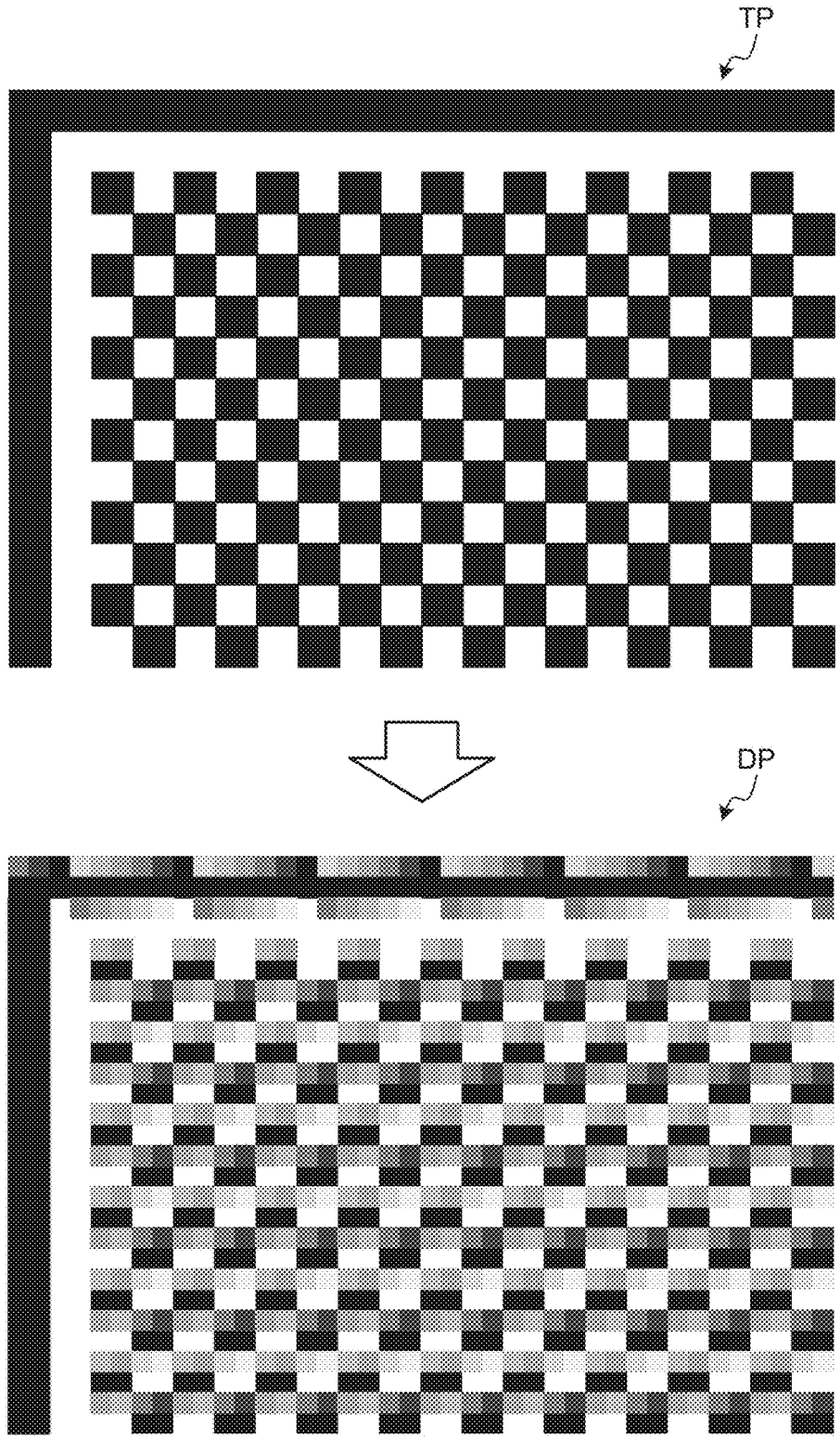
FIG. 13 illustrates a diagram illustrating an image schematically indicating detection results of the detection device of the comparative example.
Figure 14:
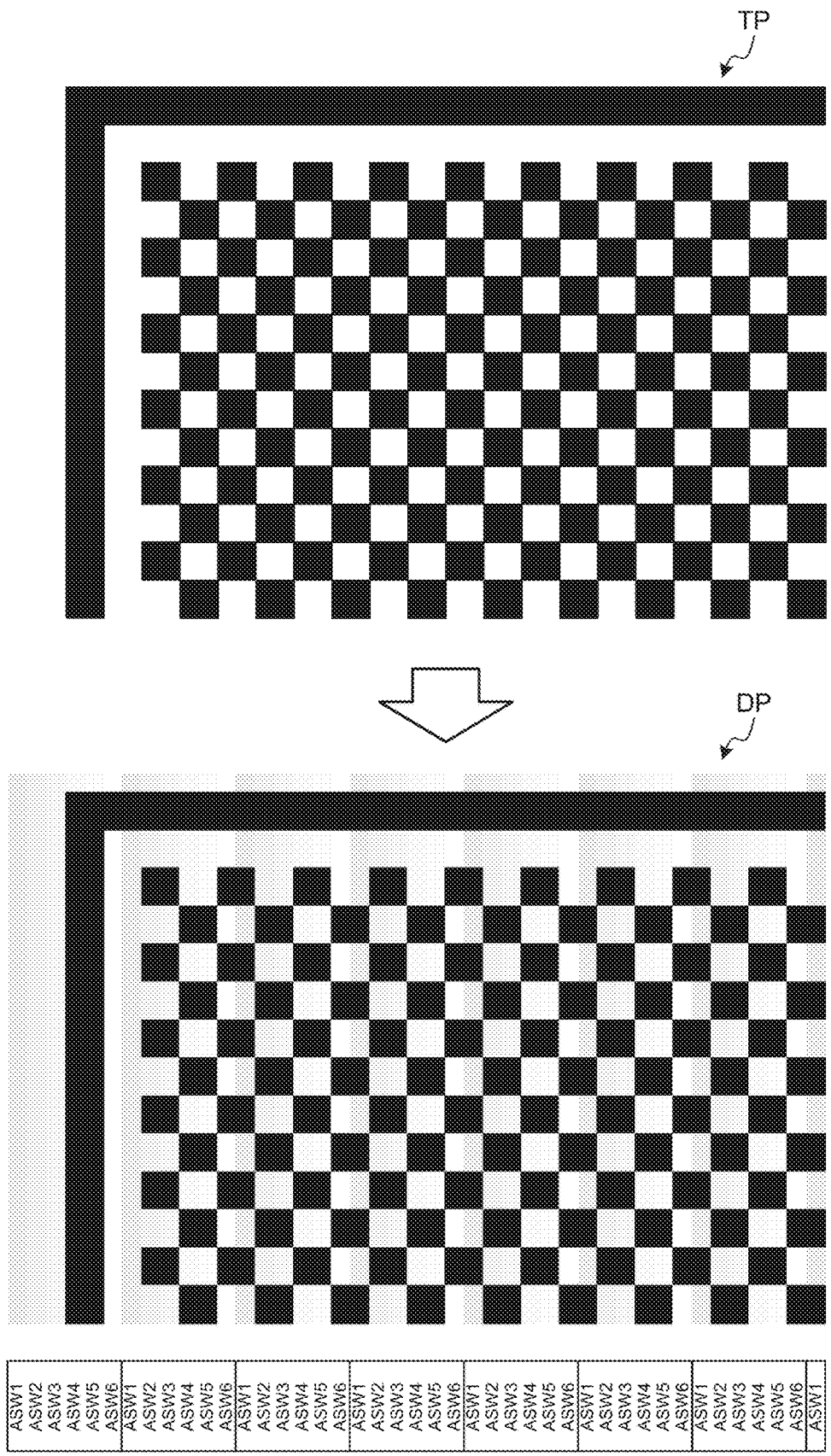
FIG. 14 illustrates a diagram illustrating the detection results of the detection device of an example.

FIG. 13 illustrates a diagram illustrating an image schematically indicating the detection results of the detection device of the comparative example. FIG. 14 illustrates a diagram illustrating an image schematically indicating the detection results of the detection device of an example. FIGS. 13 and 14 illustrate image data obtained by detecting the same test pattern TP, and both figures illustrate the test pattern TP in which black quadrilateral patterns are arranged in a staggered manner.

In a detection pattern DP of the comparative example illustrated in FIG. 13, boundaries (contrast) between black patterns and white patterns are blurred. On the other hand, in the detection pattern DP of the example illustrated in FIG. 14, the boundaries (contrast) between the black patterns and the white patterns are clear between adjacent rows. This comparison demonstrates that the detection accuracy can be improved by supplying the reset potential to the optical sensors PD and the signal lines SGL for each of the row reading periods VR as described above.

Second Modification

In the first embodiment described above, although interference of detection signals between rows can be reduced, time lag occurs from the time (for example, time t21) when the gate drive signal Vgcl(1) is set to the high-level voltage to the time of reading each column, as illustrated in FIG. 12. The exposure period Pex-6 of the optical sensor PD coupled to the signal line SGL(6) is longer than the exposure period Pex-1 of the optical sensor PD coupled to the signal line SGL(1). As a result, the detection variations may periodically occur in the column direction.

Figure 15:
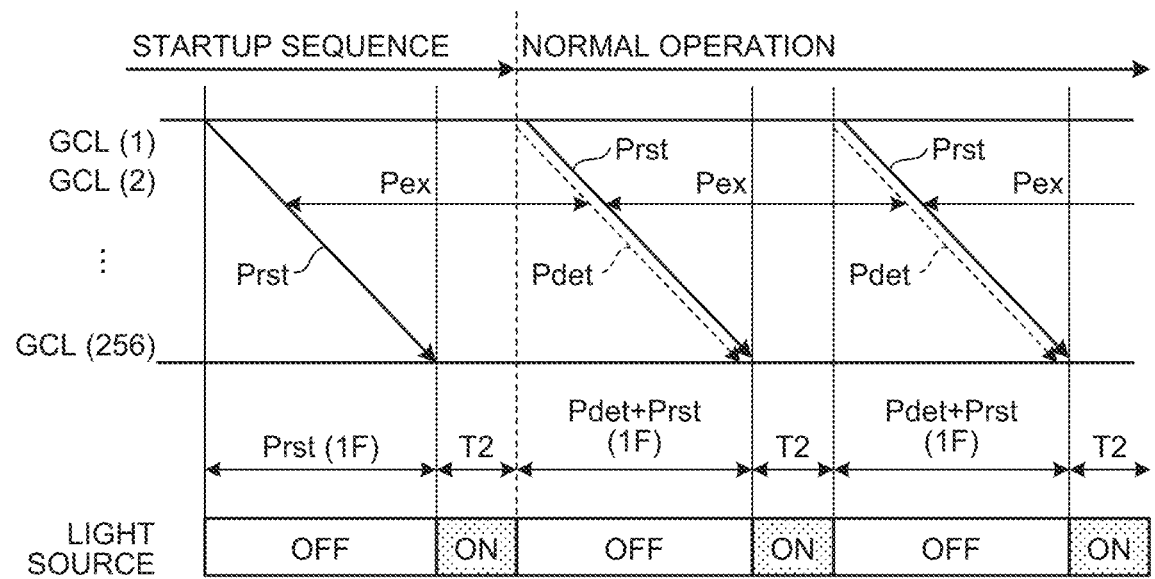
FIG. 15 is an explanatory diagram for explaining a relation between the driving of the sensor of a detection device of a second modification and the lighting operation of the light sources thereof.
Figure 16:
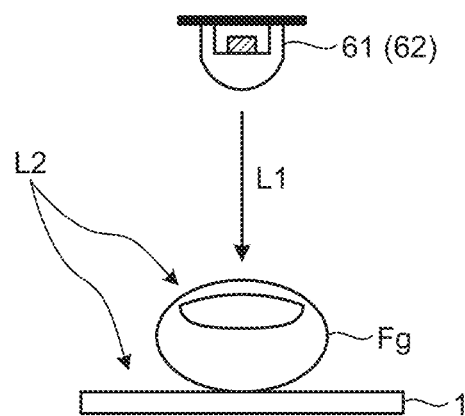
FIG. 16 is an explanatory diagram schematically illustrating a relation between the detection device of the second modification and the light sources thereof.

FIG. 15 is an explanatory diagram for explaining a relation between the driving of the sensor of a detection device of a second modification and the lighting operation of the light sources thereof. FIG. 16 is an explanatory diagram schematically illustrating a relation between the detection device of the second modification and the light sources thereof.

As illustrated in FIG. 15, the control circuit 122 causes the light sources (first light sources 61 or second light sources 62) to be off during the reset period Prst and the reading period Pdet for one frame (1F), and caused the light sources to be on during a period T2 between frames. During the period T2, none of the gate lines GCL is selected (the gate drive signal Vgcl is at the low-level voltage). That is, the light sources are off during the row reading period VR in which the first switching elements Tr of the predetermined row are in the coupled state, and the light sources are on during the period T2 in which all the first switching elements Tr are in the non-coupled state.

As a result, the light L1 (refer to FIG. 16) is not emitted from the light sources during the row reading period VR in which the gate drive signal Vgcl is at the high-level voltage. Therefore, the detection variations between columns that would be caused by the variations in the exposure periods Pex-1, . . . , Pex-6 can be reduced.

Second Embodiment

In the second embodiment, driving for further improving the detection accuracy is performed. For example, depending on the use conditions of the detection device 1, the detection device 1 may be irradiated with extraneous light L2 in addition to the light L1 from the light sources, as illustrated in FIG. 16. In this case, the sensor is irradiated with light even when the light sources are not off, and the influence of the irradiation with the extraneous light L2 differs between columns due to the difference in reading time between the columns. Therefore, if the sensor is irradiated with the extraneous light L2 during the row reading period VR, the detection variations between columns may occur.

Figure 17:
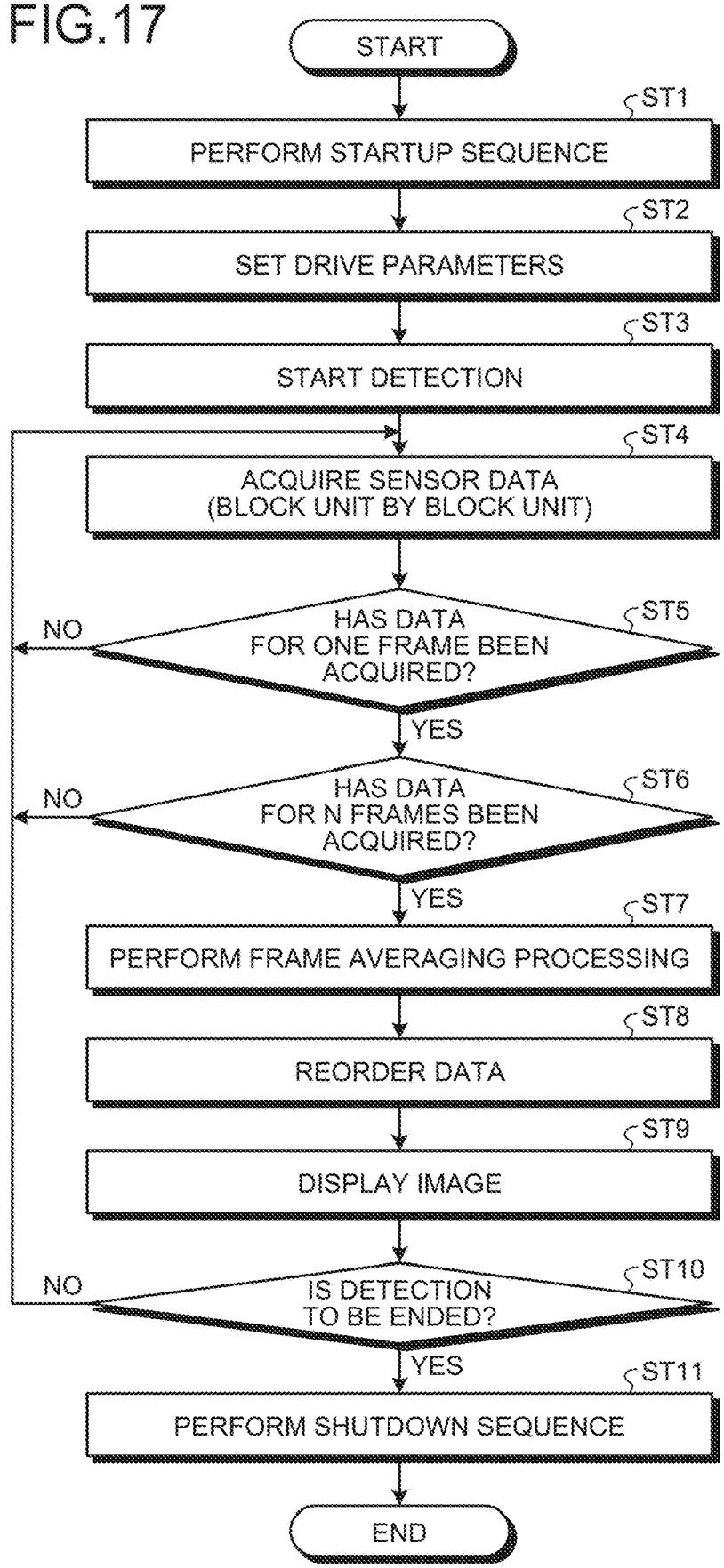
FIG. 17 is a flowchart illustrating an operation example of the detection device according to a second embodiment

FIG. 17 is a flowchart illustrating an operation example of the detection device according to the second embodiment. FIG. 18 is a table illustrating orders of coupling of the signal lines for each of the one frame detections.

As illustrated in FIG. 17, the control circuit 122 performs the startup sequence (refer to FIG. 11) of detection device 1 (Step ST1). The control circuit 122 sets drive parameters of the detection device 1 (Step ST2). The drive parameters are, for example, the sensor resolution, the number of the signal lines SGL to be selected, and the luminance of the light sources.

The control circuit 122 starts the detection (Step ST3). In the same manner as in the first embodiment described above, the control circuit 122 supplies the reset potential to the optical sensors PD and the signal lines SGL for each of the row reading periods VR.

The control circuit 122 scans the gate lines GCL and the signal lines SGL to acquire sensor data (detection signals Vdet) for each of the block units PAG (refer to FIG. 3) (Step ST4).

If data for one frame (1F) has not been acquired (No at Step ST5), the control circuit 122 continues to scan the gate lines GCL and the signal lines SGL. If the data for one frame (1F) has been acquired (Yes at Step ST5), the control circuit 122 performs the one frame detection for the next frame.

FIG. 18 illustrates the order of the selection signals ASW from the period T11 to the period T16 for each frame, for the detection of frame 1 to frame 6. As illustrated in FIG. 18, the control circuit 122 changes the order of the selection signals ASW for each frame. That is, the signal line selection circuit 16 changes the order of coupling between the signal lines SGL and the detection circuit 48 in the reading period Pdet for each of the one frame detections based on the selection signals ASW from the control circuit 122.

In other words, the length of the exposure period Pex for each column differs between frames. For example, focusing on the selection signal ASW1, the period (among the periods T11 to T16) during which the selection signal ASW1 is supplied differs between frames from frame 1 to frame 6. That is, in the example illustrated in FIG. 18, the exposure period Pex-1 according to the selection signal ASW1 (refer to FIG. 12) is shortest in frame 1 and longest in frame 2. Then, the exposure period Pex-1 (selection signal ASW1) is gradually shortened from frame 3 to frame 6.

In FIG. 18, the order of the selection signals ASW (from the period T11 to the period T16) is shifted one by one from frame 1 to frame 6. However, the order of the selection signals ASW is not limited to being changed in this way, and may be randomly changed for each frame.

Then, if the data for N frames (for example, N=6) has not been acquired (No at Step ST6), the control circuit 122 repeats Step ST4 and Step ST5. If the data for N frames has been acquired (Yes at Step ST6), the control circuit 122 performs frame averaging processing (Step ST7).

The frame averaging processing is signal processing of averaging the data (detection signals Vdet) acquired column by column for the respective frames from frame 1 to frame 6 illustrated in FIG. 18. For example, six signals detected from the signal line SGL(1) based on the selection signal ASW1 from frame 1 to frame 6 are averaged. In the same manner, signals detected column by column (on a per signal line SGL basis) are averaged. This processing can reduce the column-by-column variation of the exposure period Pex.

The control circuit 122 reorders the averaged data in the order of the columns (signal lines SGL) (Step ST8). The control circuit 122 displays an image as two-dimensional information based on the information averaged over the frames (Step ST9).

If the control circuit 122 continues the detection (No at Step ST10), the control circuit 122 repeats Step ST4 to Step ST9. If the control circuit 122 ends the detection (Yes at Step ST10), the control circuit 122 performs a shutdown sequence (Step ST11) to end the process.

In the present embodiment, the order of coupling between the signal lines SGL and the detection circuit 48 changes for each of the one frame detections, and the detection signals Vdet of the frames are averaged for each column. As a result, in the present embodiment, the variations in exposure time of the respective columns are averaged, so that the detection variations between columns can be reduced. The detection variations between columns can also be reduced by applying the present embodiment to the driving in the first embodiment illustrated in FIGS. 11 and 12 as well as to the driving in the first modification of the first embodiment as illustrated in FIG. 15.

Third Embodiment

Figure 19:
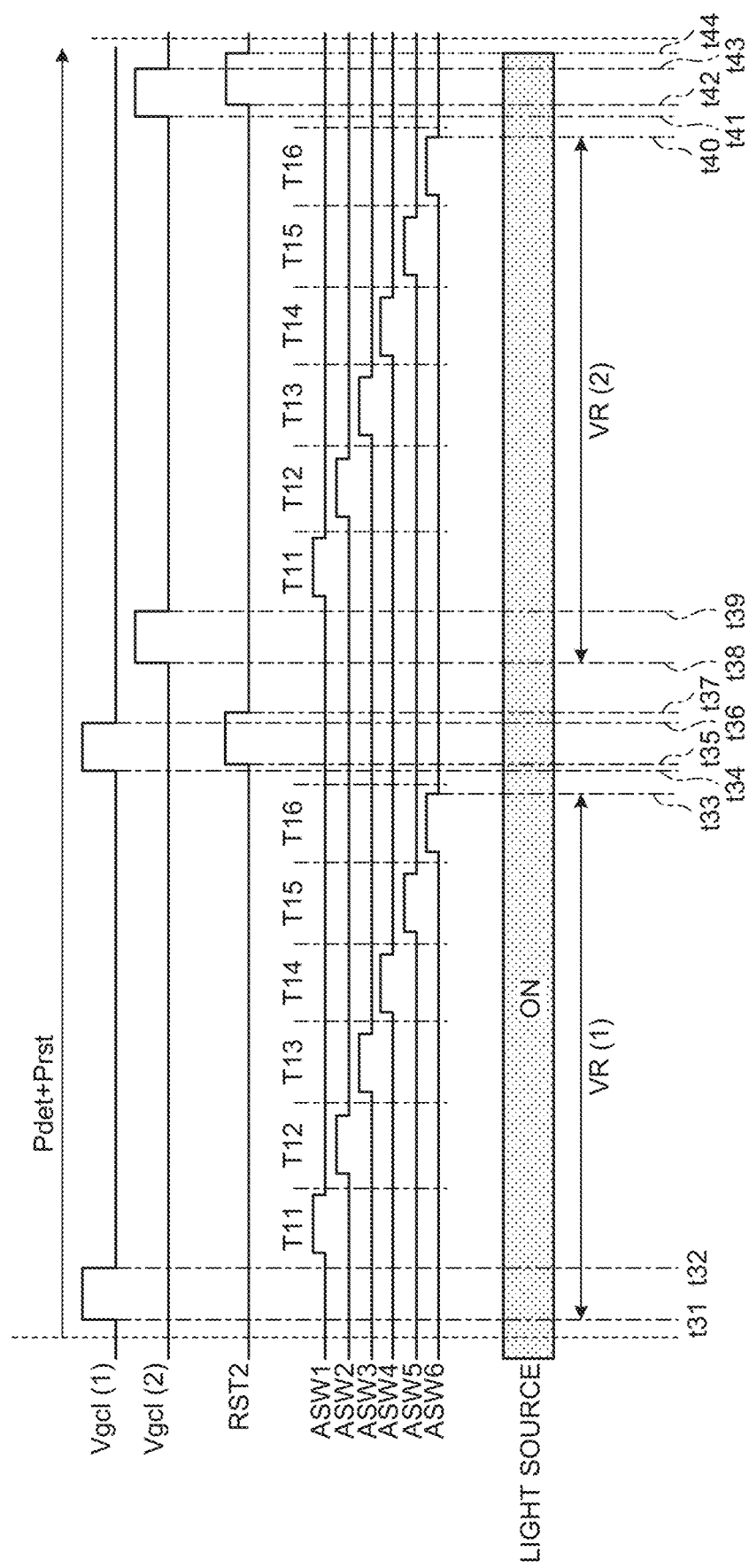
FIG. 19 is a timing waveform diagram illustrating an operation example of the detection device according to a third embodiment.

FIG. 19 is a timing waveform diagram illustrating an operation example of the detection device according to a third embodiment. The third embodiment differs from the first and the second embodiments described above in that the control circuit 122 sequentially supplies the selection signals ASW1, . . . , ASW6 to the signal line selection circuit 16 during the period in which the gate drive signal Vgcl is at the low-level voltage in the row reading period VR.

Specifically, as illustrated in FIG. 19, the gate line drive circuit 15 supplies the gate drive signal Vgcl(1) at the high-level voltage (power supply voltage VDD) to the gate line GCL(1) at time t31. The row reading period VR(1) starts when the gate drive signal Vgcl(1) is set to the high-level voltage.

At time t32 after a predetermined period has elapsed and before the selection signal ASW is supplied, the gate line drive circuit 15 sets the gate drive signal Vgcl(1) to the low-level voltage. That is, the first switching elements Tr of a predetermined row are brought into the coupled state at time t31 during the reading period of the predetermined row (row reading period VR(1)), and brought into the non-coupled state at time t32 after the predetermined period has elapsed.

During the period in which the first switching elements Tr are in the coupled state (time t31 to time t32), the selection signal ASW is not supplied, and the third switching elements TrS are in the non-coupled state. As a result, the signal line capacitor Cc is also charged with part of the electric charge stored in the capacitive element Ca corresponding to the light irradiating the optical sensor PD, according to a capacitance ratio between the capacitive element Ca and the signal line capacitor Cc.

Then, the control circuit 122 sequentially supplies the selection signals ASW1, . . . , ASW6 to the signal line selection circuit 16 during a period in which the gate drive signal Vgcl(1) is at the low-level voltage. The third switching elements TrS are sequentially brought into the coupled state according to the selection signals ASW1, . . . , ASW6. That is, during the period of reading each row (row reading period VR(1)), the first switching elements Tr of the predetermined row are in the non-coupled state, and the signal line selection circuit 16 couples the signal lines SGL to the detection circuit 48 in a predetermined order. As a result, the detection signal Vdet for each of the partial detection areas PAA is supplied to the detection circuit 48.

In the present embodiment, since each of the first switching elements Tr is in the non-coupled state during the periods T11, . . . , T16, the detection circuit 48 is not coupled to the capacitive element Ca. Therefore, during the periods T11, . . . , T16, a signal corresponding to the electric charge stored in the signal line capacitor Cc during the period in which the first switching element Tr is in the coupled state, is output as the detection signal Vdet.

When capacitance C1 denotes a capacitance value of the capacitive element Ca and capacitance C2 denotes a capacitance value of the signal line capacitor Cc, the control circuit 122 adjusts the sensor output based on the ratio between the capacitance C1 and the capacitance C2 given in Expression (1) below. Thus, the control circuit 122 can adjust the sensor output to a signal equivalent to the detection signal Vdet read by the first switching element Tr in the coupled state described in the first embodiment. As an example of the adjustment, a detection value read by the A/D converter 43 illustrated in FIG. 4 is multiplied by a value obtained by Expression (1) below.

$$(C1+C2)/C2 \qquad (1)$$

In FIG. 19, the selection signals ASW1, . . . , ASW6 are supplied in the order of the periods T11, . . . , T16 in a time-division manner. At time t33, the control circuit 122 sets the selection signal ASW6 to the low-level voltage, and the reading of the last column ends. That is, in the present embodiment, the row reading period VR(1) starts at time t31 when the gate drive signal Vgcl(1) is set to the high-level voltage, and the selection signals ASW1, ASW6 are supplied after the gate drive signal Vgcl(1) is set to the low-level voltage. The row reading period VR(1) ends when the gate drive signal Vgcl(1) is at the low-level voltage and the selection signal ASW6 for the last column changes to the low-level voltage.

At time t34, the gate line drive circuit 15 supplies the gate drive signal Vgcl(1) at the high-level voltage (power supply voltage VDD) to the gate line GCL(1). That is, after the completion of the reading period VR(1) and before the start of the reading period VR(2) of the row (second row) next to the predetermined row (first row), the first switching elements Tr of the predetermined row (first row) are brought into the coupled state.

At time t35, the control circuit 122 supplies the reset signal RST2 to the reset signal line Lrst. This operation turns on the fourth switching elements TrR to supply the reference signal COM to the optical sensors PD and the signal lines SGL corresponding to the gate line GCL(1).

Then, at time t36, the gate line drive circuit 15 sets the gate drive signal Vgcl(1) to the low-level voltage. At time t37, the control circuit 122 sets the reset signal RST2 to the low-level voltage. With this operation, the reading period Pdet and reset period Prst of the first row end.

Then, at time t38, the gate line drive circuit 15 supplies the gate drive signal Vgcl(2) at the high-level voltage (power supply voltage VDD) to the gate line GCL(2) of the second row. Subsequently, in the same manner as in the first row, the reading period Pdet and the reset period Prst of the second row are executed from time t39 to time t43. The one frame detection can be performed by repeating this operation to the last row (gate line GCL(256)).

As described above, in the third embodiment, during the period (from time t32 to time t34) in which the first switching elements Tr of the predetermined row are in the non-coupled state, the selection signals ASW1, . . . , ASW6 are sequentially supplied to perform the reading of each column. This operation can reduce the variations in the detection signal Vdet caused by the variations in exposure time of the columns. That is, in the third embodiment, the periodic difference in contrast in the row direction can be reduced as illustrated in FIGS. 13 and 14.

While the preferred embodiments of the present disclosure have been described above, the present disclosure is not limited to the embodiments described above. The content disclosed in the embodiments is merely an example, and can be variously modified within the scope not departing from the gist of the present disclosure. Any modifications appropriately made within the scope not departing from the gist of the present disclosure also naturally belong to the technical scope of the present disclosure. At least one of various omissions, substitutions, and changes of the components can be made without departing from the gist of the embodiments and the modifications described above.

What is claimed is:

1. A detection device comprising:
a plurality of optical sensors arranged in a matrix having a row-column configuration;
a plurality of switching elements, a plurality of gate lines, and a plurality of signal lines provided corresponding to the optical sensors;
a detection circuit configured to be supplied with signals from the optical sensors through the signal lines; and
a signal line selection circuit configured to switch a coupling state between the signal lines and the detection circuit, wherein
a drive signal is supplied to the gate lines row by row to bring the switching elements belonging to a predetermined row into a coupled state,
the signal line selection circuit is configured to couple the signal lines to the detection circuit column by column in a predetermined order in a reading period of the predetermined row, and
a reset potential is supplied to the optical sensors and the signal lines belonging to the predetermined row after completion of the reading period of the predetermined row and before start of the reading period of a row next to the predetermined row.

2. The detection device according to claim 1, wherein
the signal line selection circuit is configured to couple the signal lines to the detection circuit column by column in the predetermined order when the switching elements of the predetermined row are in the coupled state in the reading period of the predetermined row, and
the switching elements of the predetermined row are configured to be brought into a non-coupled state after the completion of the reading period of the predetermined row.

3. The detection device according to claim 1, wherein
the switching elements of the predetermined row are configured to be in the coupled state in the reading period of the predetermined row and to be brought into a non-coupled state after a predetermined period has elapsed,
the signal line selection circuit is configured to couple the signal lines to the detection circuit column by column in the predetermined order when the switching elements of the predetermined row are in the non-coupled state, and
the switching elements of the predetermined row are configured to be brought into the coupled state and the reset potential is supplied to the optical sensors and the signal lines belonging to the predetermined row, after the completion of the reading period and before the start of the reading period of the row next to the predetermined row.

4. The detection device according to claim 3, wherein the signals from the optical sensors are adjusted based on a ratio of sensor capacitance generated in the optical sensors and signal line capacitance generated in the signal lines.

5. The detection device according to claim 1, wherein the signal line selection circuit is configured to change an order of coupling between the signal lines and the detection circuit in the reading period on a one frame detection by one frame detection basis.

6. A fingerprint detection device comprising:
the detection device according to claim 1; and
at least one or more light sources.

7. A vein detection device comprising:
the detection device according to claim 1; and
at least one or more light sources.

* * * * *